US012575839B2

(12) United States Patent
Sayger

(10) Patent No.: US 12,575,839 B2
(45) Date of Patent: Mar. 17, 2026

(54) SYSTEMS AND METHODS FOR BONE FIXATION

(71) Applicant: Crossroads Extremity Systems, LLC, Memphis, TN (US)

(72) Inventor: Daniel Sayger, Southaven, MS (US)

(73) Assignee: Crossroads Extremity Systems, LLC, Memphis, TN (US)

( * ) Notice: Subject to any disclaimer, the term of this patent is extended or adjusted under 35 U.S.C. 154(b) by 438 days.

(21) Appl. No.: 17/934,231

(22) Filed: Sep. 22, 2022

(65) Prior Publication Data

US 2023/0086330 A1      Mar. 23, 2023

Related U.S. Application Data

(60) Provisional application No. 63/247,231, filed on Sep. 22, 2021.

(51) Int. Cl.
  *A61B 17/17*        (2006.01)
  *A61B 17/14*        (2006.01)
        (Continued)

(52) U.S. Cl.
  CPC .............. *A61B 17/17* (2013.01); *A61B 17/15* (2013.01); *A61B 17/14* (2013.01); *A61B 17/142* (2016.11); *A61B 17/151* (2013.01); *A61B 17/1604* (2013.01); *A61B 17/1615* (2013.01); *A61B 17/162* (2013.01); *A61B 17/1633* (2013.01);
        (Continued)

(58) Field of Classification Search
  CPC ....... A61B 17/17; A61B 17/151; A61B 17/15; A61B 17/1604; A61B 17/1682; A61B 17/1775; A61B 17/8866; A61B 17/1615; A61B 17/1703; A61B 17/1728; A61B 17/1732; A61B 17/1735; A61B 17/1739; A61B 17/1782; A61B 17/152; A61B 17/162; A61B 17/1633; A61B 17/1642; A61B 17/1657; A61B 17/1659; A61B 17/14; A61B 17/142; A61B 17/147; A61B 17/1637; A61B 2017/564
  USPC .............. 606/86 R, 75, 79, 167–189, 82, 85, 606/96–98, 915, 916
  See application file for complete search history.

(56) References Cited

U.S. PATENT DOCUMENTS

| | | | | |
|---|---|---|---|---|
| 2,837,939 A | * | 6/1958 | Leitner ................ | B25H 1/0078 408/110 |
| 4,082,474 A | * | 4/1978 | Stiger .................. | B25H 1/0078 408/110 |

(Continued)

FOREIGN PATENT DOCUMENTS

EP            1393696 A1      3/2004

*Primary Examiner* — Marcela I. Shirsat
(74) *Attorney, Agent, or Firm* — BakerHostetler

(57)            ABSTRACT

A system for providing fixation of first and second bones includes a drill guide that receives a drill bit to create first and second holes in the first and second bones, respectively. Guide pins can be driven into the first and second holes. The guide pins are received by a surgical saw to guide the surgical saw toward a joint between the first and second bones, thereby creating a third hole in each of the bones across the joint. The guide pins are then removed, and an implant can be inserted into the bones, such that a first leg of the implant is disposed in the first hole, a second leg of the implant is disposed in the second hole, and a keel of the implant is disposed in the third hole.

16 Claims, 20 Drawing Sheets

(51) Int. Cl.

| | |
|---|---|
| *A61B 17/15* | (2006.01) |
| *A61B 17/16* | (2006.01) |
| *A61B 17/56* | (2006.01) |

(52) U.S. Cl.
CPC ....... *A61B 17/1657* (2013.01); *A61B 17/1659* (2013.01); *A61B 17/1682* (2013.01); *A61B 17/1703* (2013.01); *A61B 17/1728* (2013.01); *A61B 17/1732* (2013.01); *A61B 17/1735* (2013.01); *A61B 17/1739* (2013.01); *A61B 17/1775* (2016.11); *A61B 2017/564* (2013.01)

(56) References Cited

U.S. PATENT DOCUMENTS

| | | | |
|---|---|---|---|
| 11,179,149 B2 | 11/2021 | Hartdegen et al. | |
| 2004/0039394 A1 | 2/2004 | Conti et al. | |
| 2017/0000537 A1* | 1/2017 | Fallin | A61B 17/808 |
| 2018/0140308 A1* | 5/2018 | Anderson | B23B 49/02 |
| 2018/0146970 A1* | 5/2018 | Luna | A61F 2/4202 |
| 2018/0353172 A1* | 12/2018 | Hartdegen | A61B 17/809 |
| 2021/0022879 A1 | 1/2021 | Hollis et al. | |
| 2021/0251670 A1 | 8/2021 | Sayger et al. | |

* cited by examiner

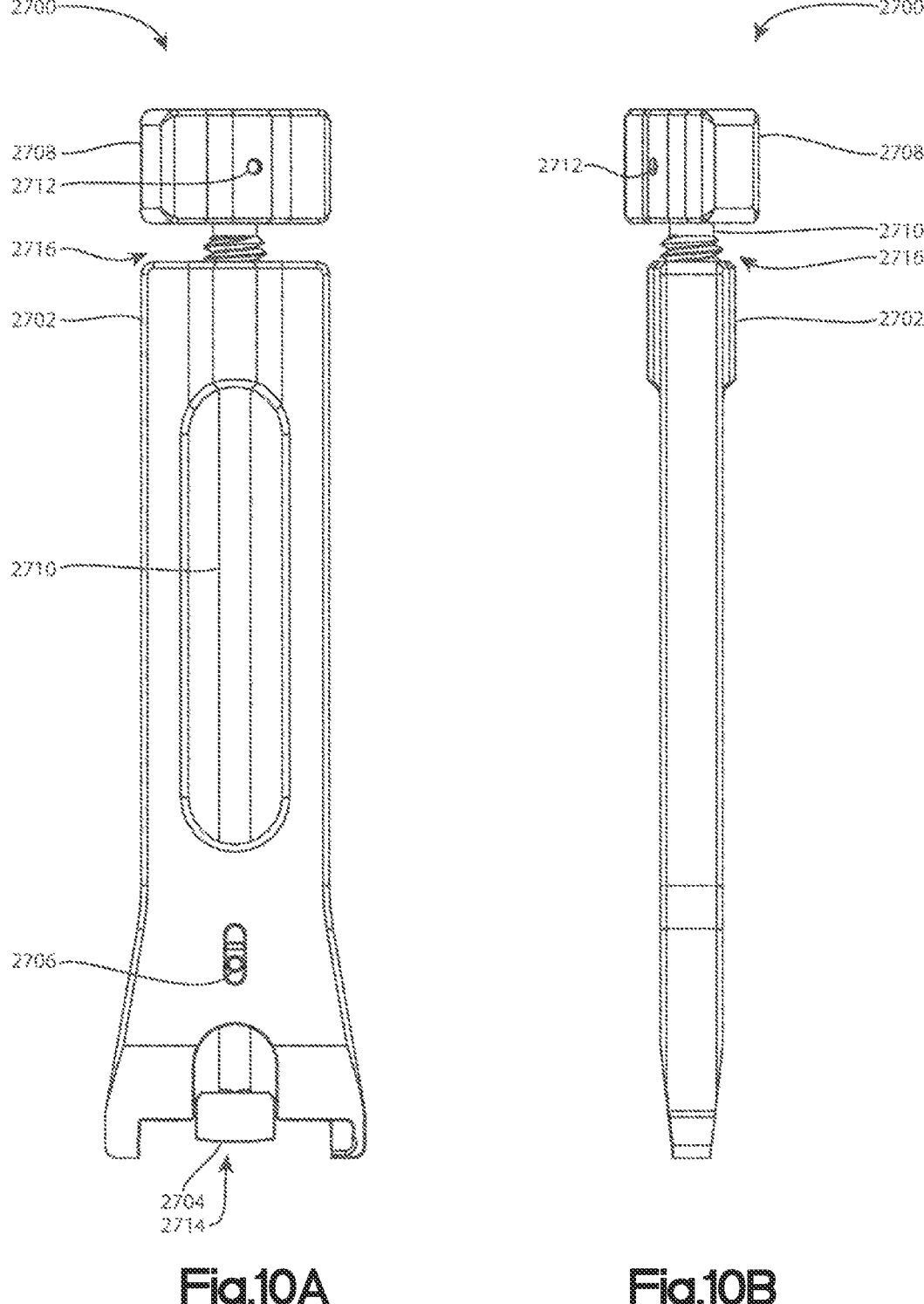
Fig.10A                    Fig.10B

SYSTEMS AND METHODS FOR BONE FIXATION

CROSS-REFERENCE TO RELATED APPLICATIONS

This claims priority to U.S. Patent Application Ser. No. 63/247,231 filed Sep. 22, 2021, the disclosure of which is hereby incorporated by reference as if set forth in its entirety herein.

FIELD

The present disclosure relates to medical devices and more particularly to systems and methods for bone fixation.

BACKGROUND

Successful bone fusion relies upon stable initial fixation of two or more bones or bone fragments. Until fusion is achieved, one or more implants must stabilize the bones or bone fragments against relative translation and/or rotation in response to forces acting across the joint or interface between the bones or bone fragments. There is a need for surgical tools the facilitate preparation of bone to receive such implants.

SUMMARY

In one example, a method is provided for joining two bones. The method can include the step of driving first and second guide pins into respective first and second bones, such that the first and second guide pins are disposed in first and second holes, respectively of the first bone. After the driving step, first and second guide pins can be inserted into respective first and second guide holes of a surgical saw, such that a saw blade of the surgical saw is aligned with a target cut location that is defined by either or both of the first and second bones. Next, movement of the surgical can be guided along the first and second guide pins to the target cut location, such that the saw blade creates an intermediate hole at the target cut location between the first and second holes. The surgical drill and the first and second guide pins can then be removed. Finally, an implant can be inserted into the first and second holes, such that a keel of the implant is inserted into the intermediate hole.

BRIEF DESCRIPTION OF THE DRAWINGS

Aspects and advantages of the embodiments provided herein are described with reference to the following detailed description in conjunction with the accompanying drawings. Throughout the drawings, reference numbers may be re-used to indicate correspondence between referenced elements. The drawings are provided to illustrate example embodiments described herein and are not intended to limit the scope of the disclosure.

FIG. 10A is a front elevation view of an implant inserter constructed in accordance with one example;

FIG. 10B is a side elevation view of the implant inserter of FIG. 10A;

DETAILED DESCRIPTION

The following description is directed to certain implementations for the purpose of describing the innovative aspects of this disclosure. However, a person having ordinary skill in the art will readily recognize that the teachings herein can be applied in a multitude of different ways.

The embodiments described herein can be manufactured from a number of different materials or combinations of materials. Nitinol, stainless steel, titanium, and/or other materials may have desirable material properties for certain components described herein. Stainless steel and/or titanium may not possess shape memory or super elasticity, but may possess the mechanical properties for embodiments that may benefit from mechanical manipulation to achieve multiple configurations. Still other materials such as PEEK or other polymers may also possess material properties beneficial for the embodiments described herein. A combination of materials may also be preferred. Those skilled in the art are aware of the typical materials and combinations of materials applicable to the current technology.

Figures 2A, 2B:
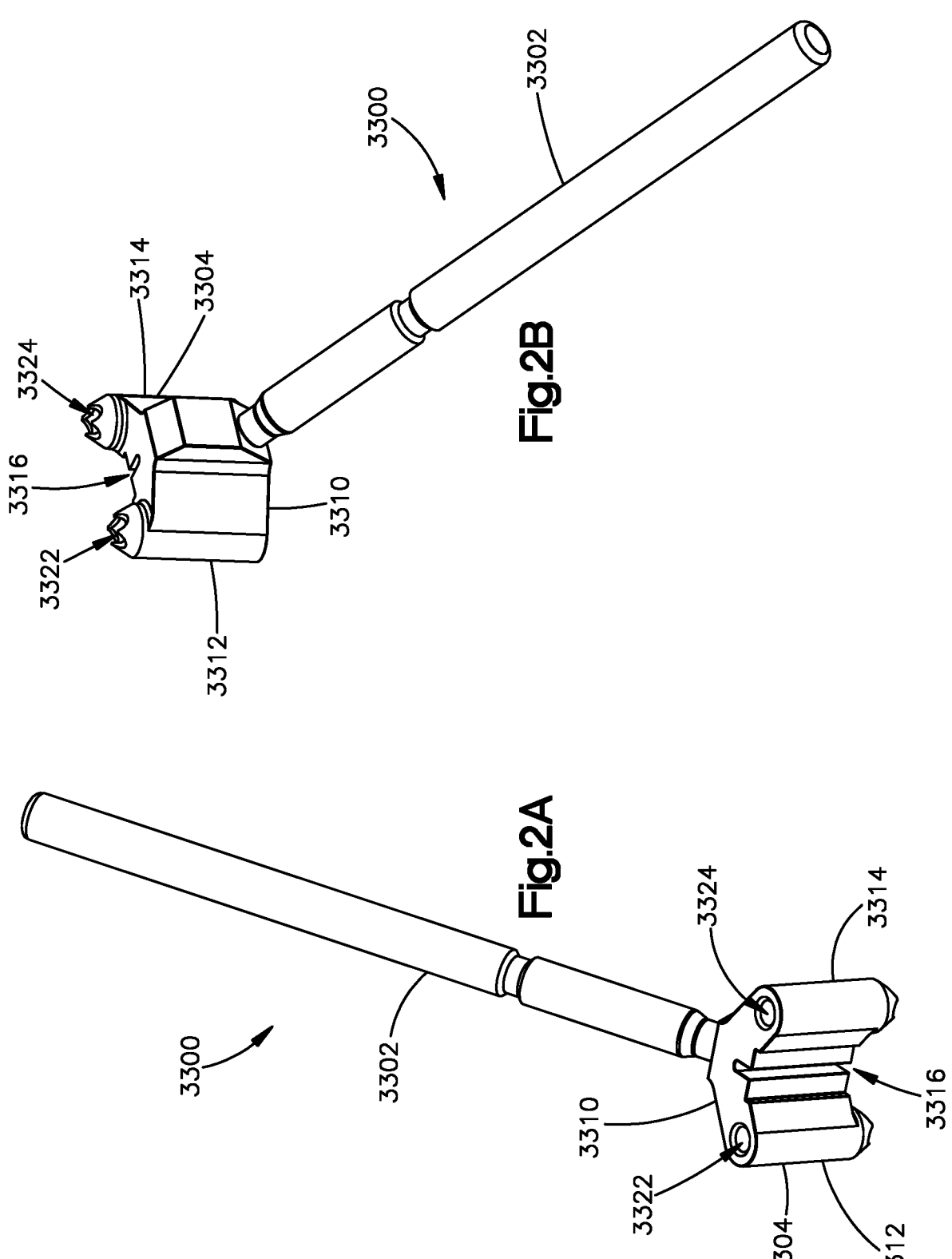
FIG. 2A is a perspective view of a drill guide assembly.
FIG. 2B is another perspective view of the drill guide assembly.

Generally described, a fixation system, devices of the fixation system, and methods of using the fixation system as described herein facilitate the preparation of bone to an implant so as to facilitate fusion of two bones. The system can include a drill guide assembly 3300 (see FIGS. 2A-2B) that can be used to create holes in the bones, guide pins 30 and 40 that are configured to be inserted into the holes (see FIG. 4), a surgical saw 240 (see FIG. 5A) configured to be guided by the guide pins 30 and 40 to create an elongate opening in at least one of the bones, and an implant 2400 (see FIG. 9A) that is configured to be inserted into the openings in the bones using an inserter 2700 (see FIG. 10A). Each of the devices and the associated methods will now be described. Further description and other embodiments of certain components of the system, including implants, drill guides, implant inserters, and drill bits suitable for use as described herein are in U.S. Patent Application Publication No. 2018/0353172, the disclosure of which is hereby incorporated by reference as if set forth in its entirety herein.

Figure 1:
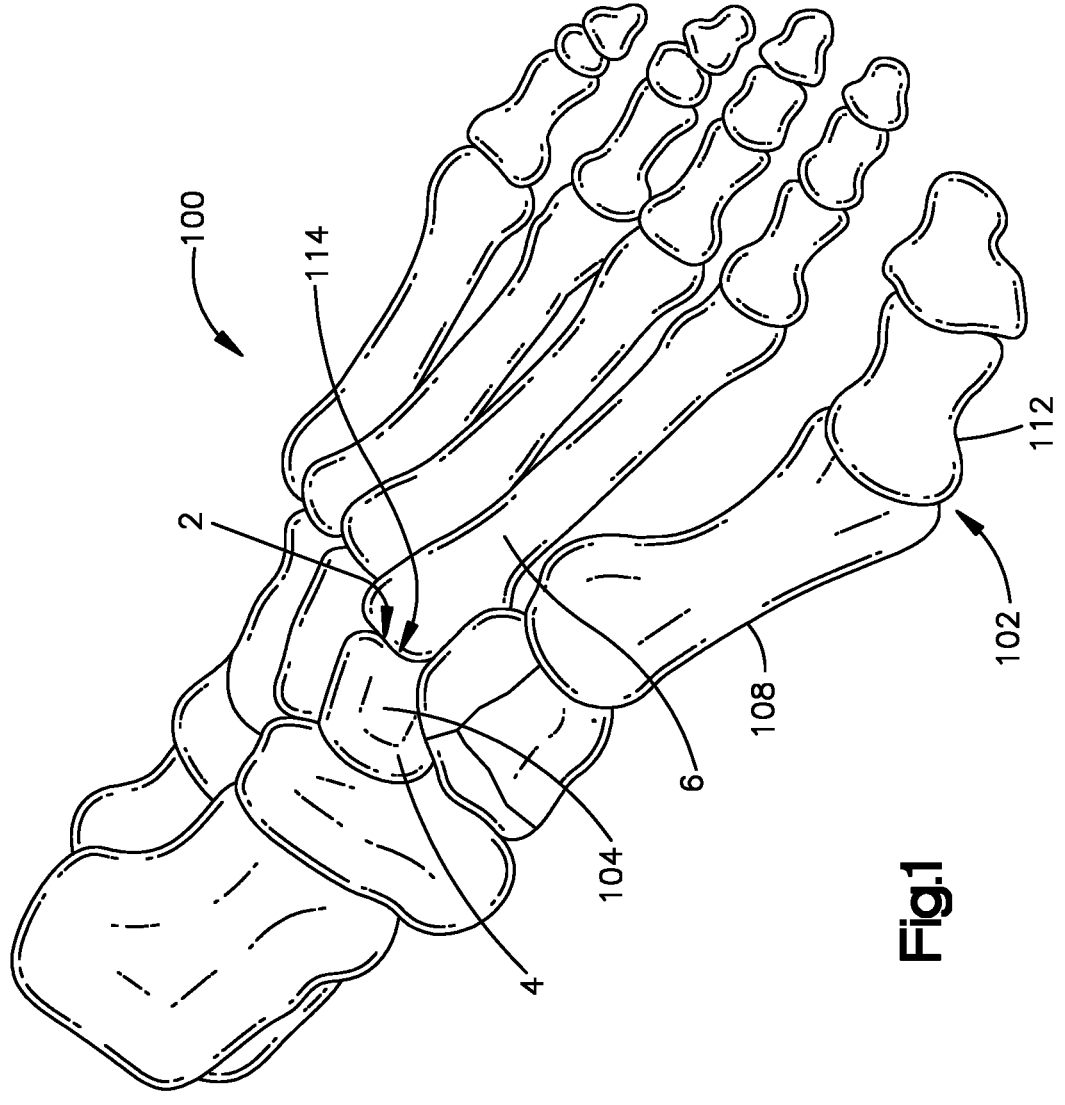
FIG. 1 is a perspective view of a patient's foot.

FIG. 1 shows a skeletal view of a patient's foot 5 having at least one of a first bone 4, a second bone 6, and a joint 2 between the first and second bones 4 and 6. In one example, the first bone 4 can be defined by a cuneiform bone 104, the second bone can be defined by a metatarsal 108, and the joint 2 can be a tarsometatarsal (TMT) joint 114 between the cuneiform bone 104 and the metatarsal 108. Thus, in one example, the second bone 6 can be disposed distal of the first bone 4. The first bone 4 can therefore be referred to as a proximal bone, and the second bone 6 can be referred to as a distal bone. While the second cuneiform bone and the second metatarsal are shown, the bones can define any cuneiform and metatarsal of the foot as desired. It is further appreciated that the first and second bones 4 and 6 are not limited to bones of the foot. In this regard, the first and second bones can be anatomically distinct bones, or can be bone fragments of the same (or a common) anatomical bone. Thus, the joint 2 can be an anatomical joint, an osteotomy, a fracture, an interface, or other discontinuity between the first and second bones 4 and 6. In some instances, it can be beneficial to provide fixation of the first and second bones 4 and 6 to each other across the joint 2, for instance when a deformity exists with one of the bones or the joint.

Referring initially to FIGS. 2A-3A, the drill guide assembly 3300 can be used to prepare holes in a first bone 4 and a second bone 6 on either side of a joint 2. The drill guide assembly 3300 can include a guide 3304 and a handle 3302 that extends from the guide 3304. For instance, the handle 3302 can be threadedly inserted into the guide 3304 so as to removably attach the handle 3302 to the guide 3304 to thereby define a rigid construct.

The drill guide 3304 includes first and second guide elements 3312 and 3314, respectively. The guide 3304 includes a first channel 3322 that extends through the first guide element 3312, and a second channel 3324 that extends through the second guide element 3314. The first and second channels 3322 and 3324 are configured to guide a drill bit 2550 (see FIG. 3B) so as to create holes in underlying bone that will receive the first and second guide pins 30 and 40 (see FIG. 4). In the example shown, the first and second channels 3322 and 3324 can be coplanar with each other. That is, the first and second channels 3322 and 3324 extend along respective central axes that are included in a common plane. In other embodiments, the channels may not be coplanar. The central axes of the first and second channels 3322 and 3324 can be oriented parallel with each other in one example. Alternatively, the central axes can be angulated with respect to each other.

Each of the first and second guide elements 3312 and 3314 can define a pointed or tapered distal tip to facilitate engagement with bone or tissues during use. The guide elements 3312 and 3314 can be carried by a generally Y- or V-shaped body 3310. The guide 3304 can define an opening 3316 that can be configured as a linear slot or alternative opening that extends through the body 3310 along the distal direction. The opening 3316 can be open to an exterior surface of the body 3310. Alternatively, the opening 3316 can be instead configured as an enclosed opening that is enclosed along its perimeter by the body 3310. The opening 3316 can be disposed equidistantly between the first and second channels 3322 and 3324.

In one example, the opening 3316 can be configured to receive a locator 3317, such as a k-wire. The locator 3317 can be driven into bone or the joint 2, such that when the locator is received in the complementary opening 3316, the drill guide assembly 3300 can oriented more such that the central axes of the first and second channels 3322 and 3324 are separated by a direction that is substantially perpendicular to the joint 2. The locator 3317 can define a location where a midpoint of a keel 2450 of the implant 2400 (see FIG. 9A) will be located when the implant 2400 is inserted. In some examples, the locator 3317 is driven into the joint 2 in a direction substantially parallel to the joint as confirmed by lateral X-Ray. The locator 3317, for instance as a k-wire, may be inserted in the joint 2 between the first and second bones 4 and 6 so that the keel 2450 will be centered across the joint 2. Further, when the drill guide assembly 3300 is perpendicular to the joint 2 the implant 2400 will similarly be oriented perpendicular to the joint 2. In some examples, the k-wire can be replaced by a bone pin, drill bit, reamer, peg, rod, shaft, dowel, and the like. In other examples, the locator 3317 can have a non-circular transverse cross section, such as an oval or rectangular cross section. This may be advantageous when the part is inserted into the joint 2, as such a part will tend to orient itself with the major cross-sectional dimension oriented along the joint 2.

Figures 3A, 3B:
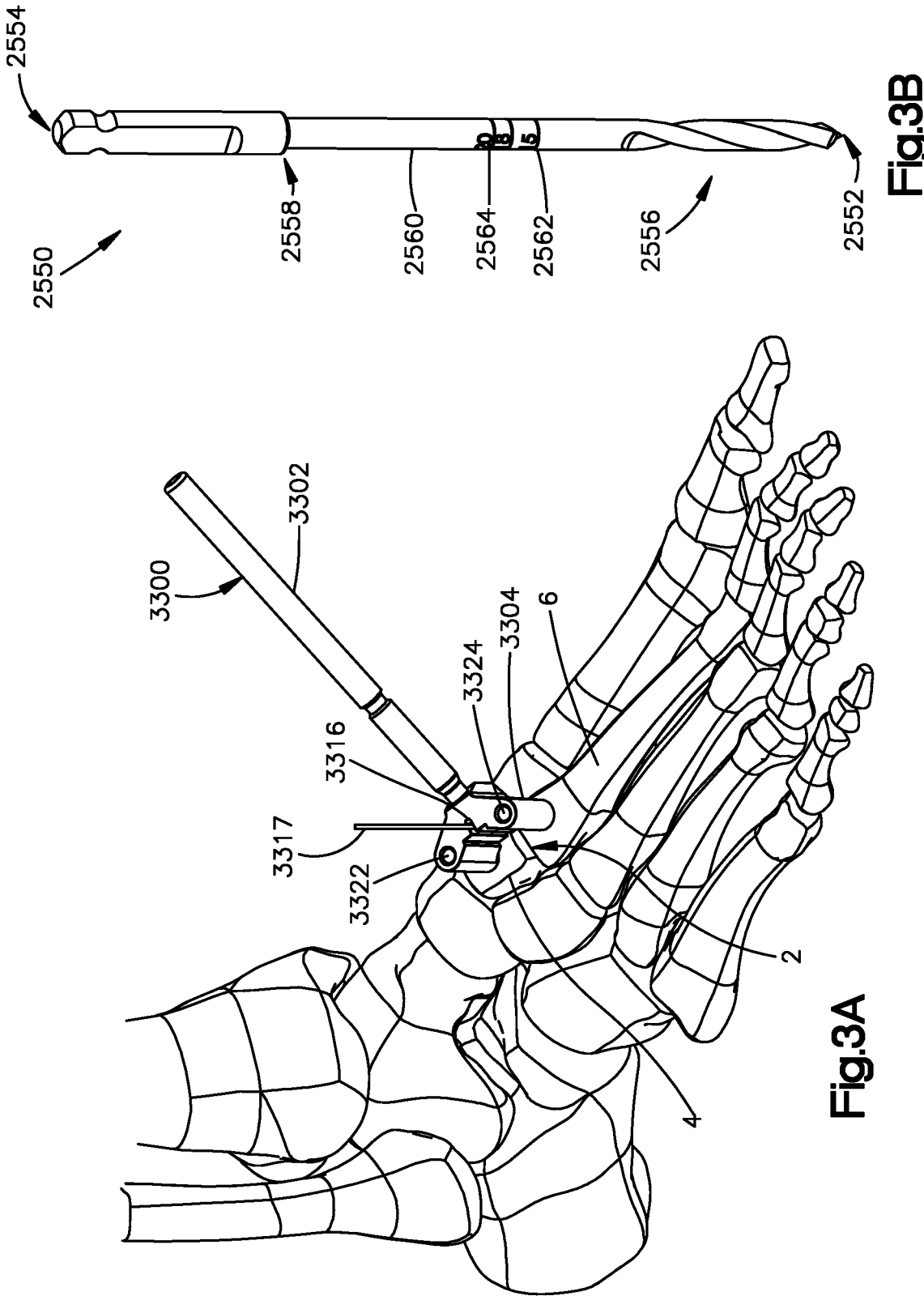
FIG. 3A is a perspective view of the drill guide of FIG. 2A shown placed against underlying first and second bones.
FIG. 3B is a perspective view of a drill bit.

Referring now to FIG. 3A in particular, the guide 3304 of the drill guide assembly 3300 is inserted using the handle 3302 such that drill guide body 3310 is aligned with or abuts the surface of either or both of the first and second bones 4 and 6. Thus, the guide 3304 can extend across the joint 2. As described above, the locator 3317 is positioned in the joint 2 along a direction substantially parallel to the joint 2. The locator 3317 can extend through the opening 3316. In one example, the locator 3317 can be driven into the joint 2, and the guide 3304 can be positioned over the locator 3317. When the locator 3317 is disposed in the opening 3316, the first channel 3322 is aligned with the first bone 4 along its central axis, and the second channel 3324 is aligned with the second bone 6 along its central axis. Further, the joint 22 can be spaced substantially equidistantly from the central axes of the first and second channels 3322 and 3324. It is recognized, of course, that the locator 3317 can be omitted in other examples. Positioning the drill guide assembly 3300 relative to the joint 2, the first and second bones 4, 6, and the locator 3317 so that the distal tip of the first guide element 3312 abuts the first bone 4, the distal tip of the second guide element 3314 can abut the second bone 6, and the opening 3316 can receive the locator 3317.

Referring now to FIG. 3B, the system can include a drill bit 2550 that can be driven through the drill guide 3304 to prepare pilot holes for implant 2400. The drill bit 2550 extends from a proximal end portion 2554 to a distal end portion 2552. The distal end portion 2552 includes a cutting portion 2556 with side and/or end cutting flutes. The proximal end portion 2554 includes a torque coupling portion 2558 for connection to a powered or manual torque source, such as an electric drill or a T-handle. The drill bit 2550 includes an intermediate portion 2560 that extends from the proximal end portion 2554 to the distal end portion 2552. In some examples, the intermediate portion 2560 can have an outer diameter that is larger than the outer diameter of the cutting portion 2556 and smaller than the outer diameter of the torque coupling portion 2558. The drill bit 2550 may include one or more depth marks and/or depth stops and/or indicia. For example, the drill bit 2550 can include a shoulder 2562 that is disposed between the cutting portion 2556 and the intermediate portion 2560. The shoulder 2562 can define a depth mark or depth stop. The drill bit 2550 can alternatively or additionally include a depth marking 2564 at the intermediate portion 2560 at a location proximal to the shoulder 2562. The shoulder 2562 and/or depth mark 2564 may align with, or may make contact with, a corresponding feature of the drill guide 3300 to indicate that the drill bit 2550 has been advanced into bone to a desired predetermined depth.

Figure 3C:
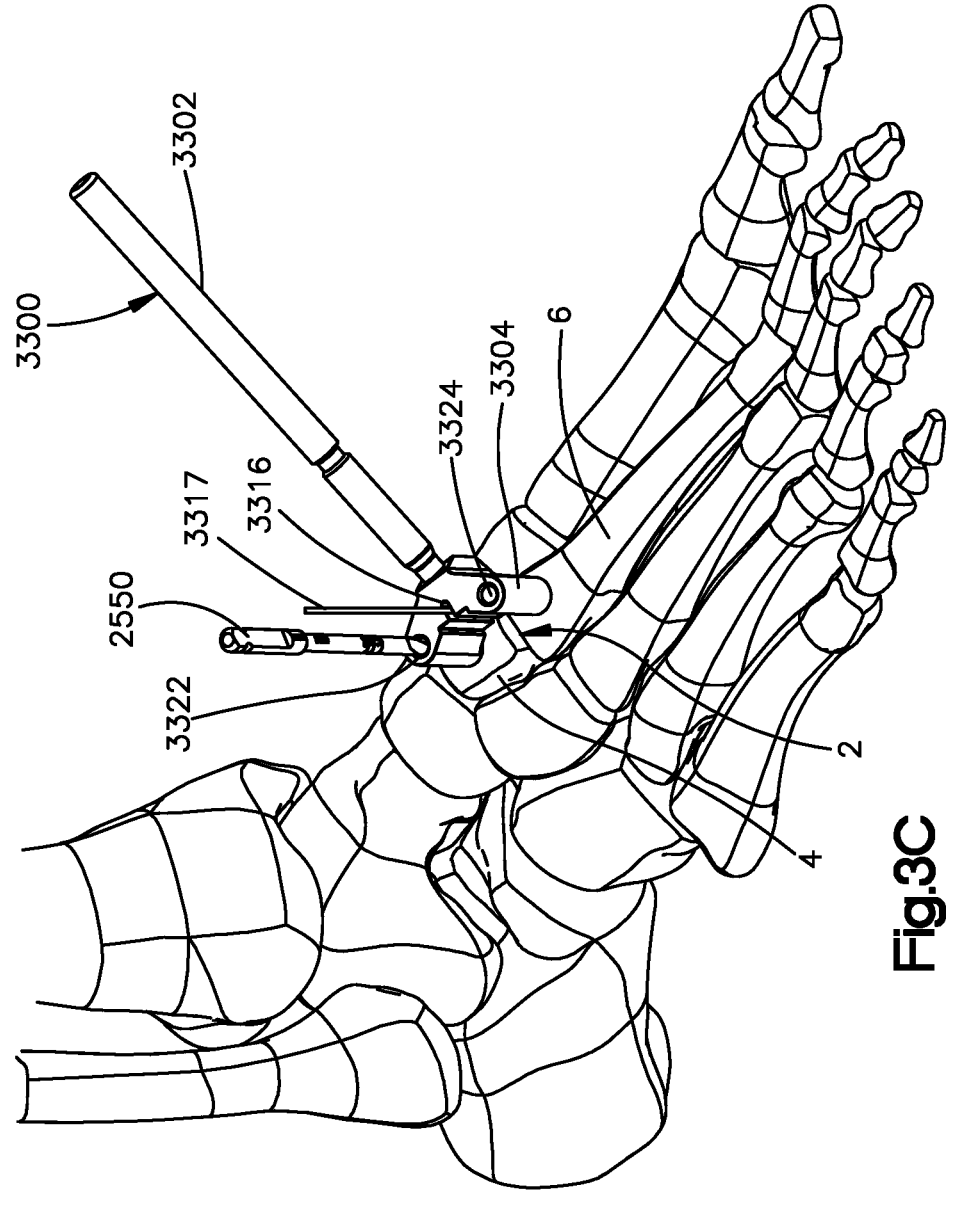
FIG. 3C is a perspective view of the drill bit of FIG. 3B driven through the drill guide to create a first hole in the first bone.

Referring now to FIG. 3C, the drill bit 2550 can be driven through the first channel 3322 of the guide 3304 and into the first bone 4. The drill bit 2550 can be driven to rotate either manually or under power from an electric drill, as desired. Thus, the cutting flutes of the drill bit 2250 can create a first or proximal hole 2492 (see FIG. 4) into the first bone 4 as the drill bit is driven into the first bone 4. The drill bit 2250 can be driven to a desired depth, so that the created hole 2492 extends into the first bone 4 at the desired depth.

Figure 3D:
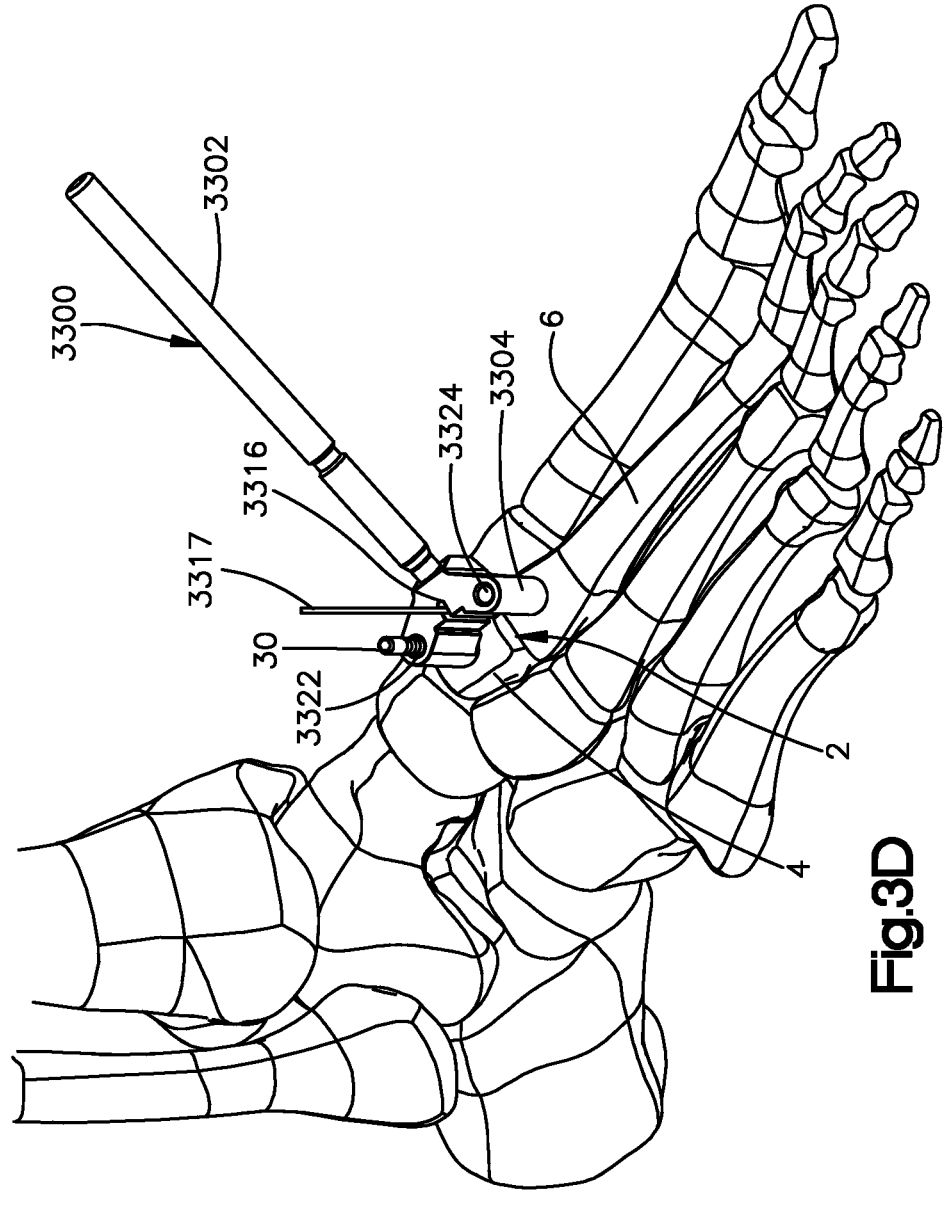
FIG. 3D is a perspective view of a first guide pin inserted into the first hole.

Referring to FIG. 3D, once the first hole 2492 (FIG. 4) has been created, a first or proximal guide pin may be inserted through first guide channel 3322 and into the first or proximal hole 2492. In particular, the drill bit 2550 can be removed from the first bone 4 and the first channel 3322. Subsequently, the first guide pin 30 can be driven through the first channel 3322 of the guide 3304 and into the first hole 2492. The guide pin 30 can be fully inserted into an entirety of the depth of the first hole 2492. In other examples, the guide 3304 can be removed from the bone 4 prior to inserting the first guide pin 30 into the first hole 2492. In this regard, the first guide pin 30 can be driven into the first hole 2492 without first being driven through the first guide channel 3322.

Figure 3E:
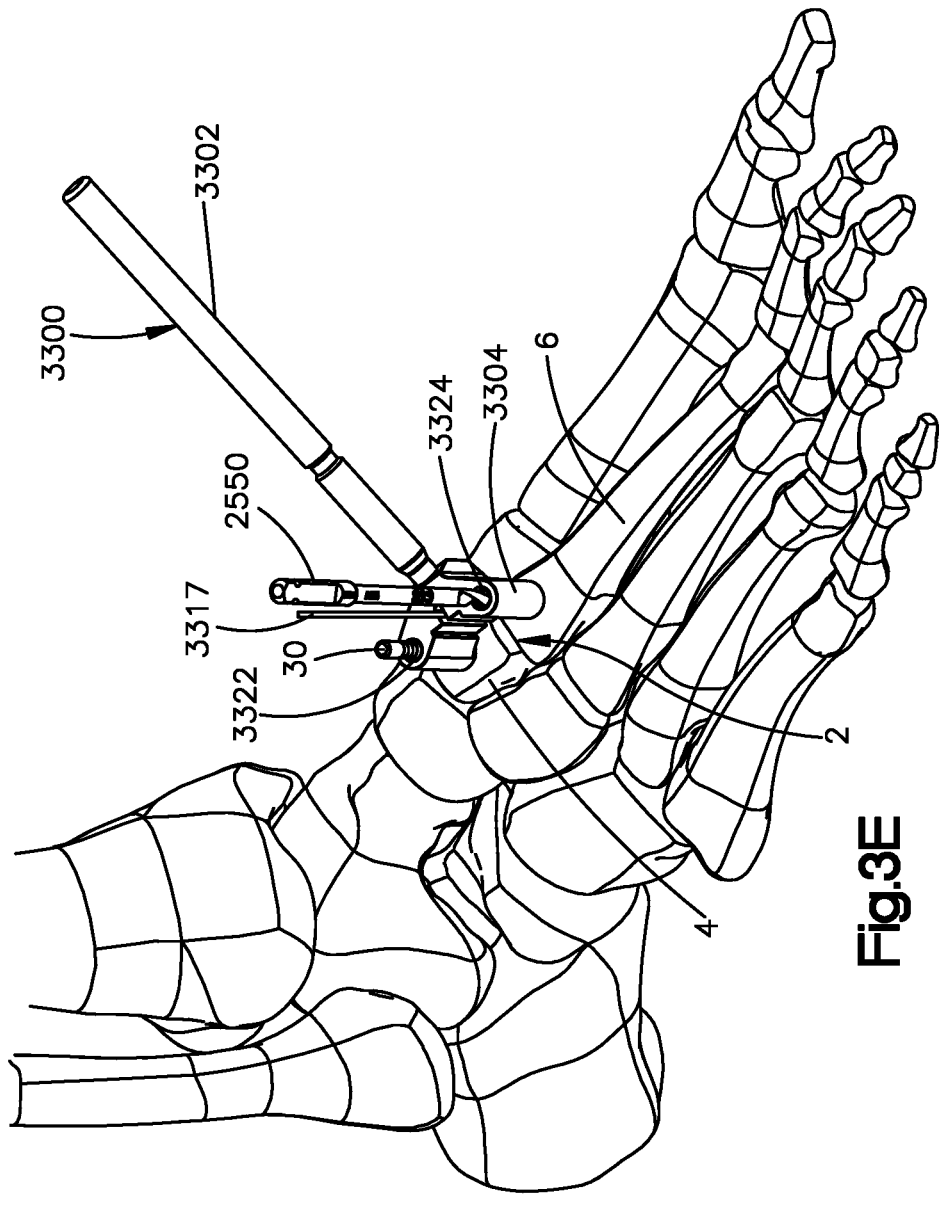
FIG. 3E is a perspective view of the drill bit driven through the drill guide to creating a second hole in the second bone.

Referring now to FIG. 3E, the drill bit 2550 can be driven through the second channel 3324 of the guide 3304 and into the second bone 6. The drill bit 2550 can be driven to rotate either manually or under power from an electric drill, as desired. Thus, the cutting flutes of the drill bit 2250 can create a second or distal hole 2494 (see FIG. 4) into the second bone 6 as the drill bit is driven into the second bone 6. The drill bit 2250 can be driven to a desired depth, so that the created second hole 2494 extends into the second bone 6 at the desired depth. The depth of the second hole 2494 can be substantially equal to the depth of the first hole 2492.

Figure 3F:
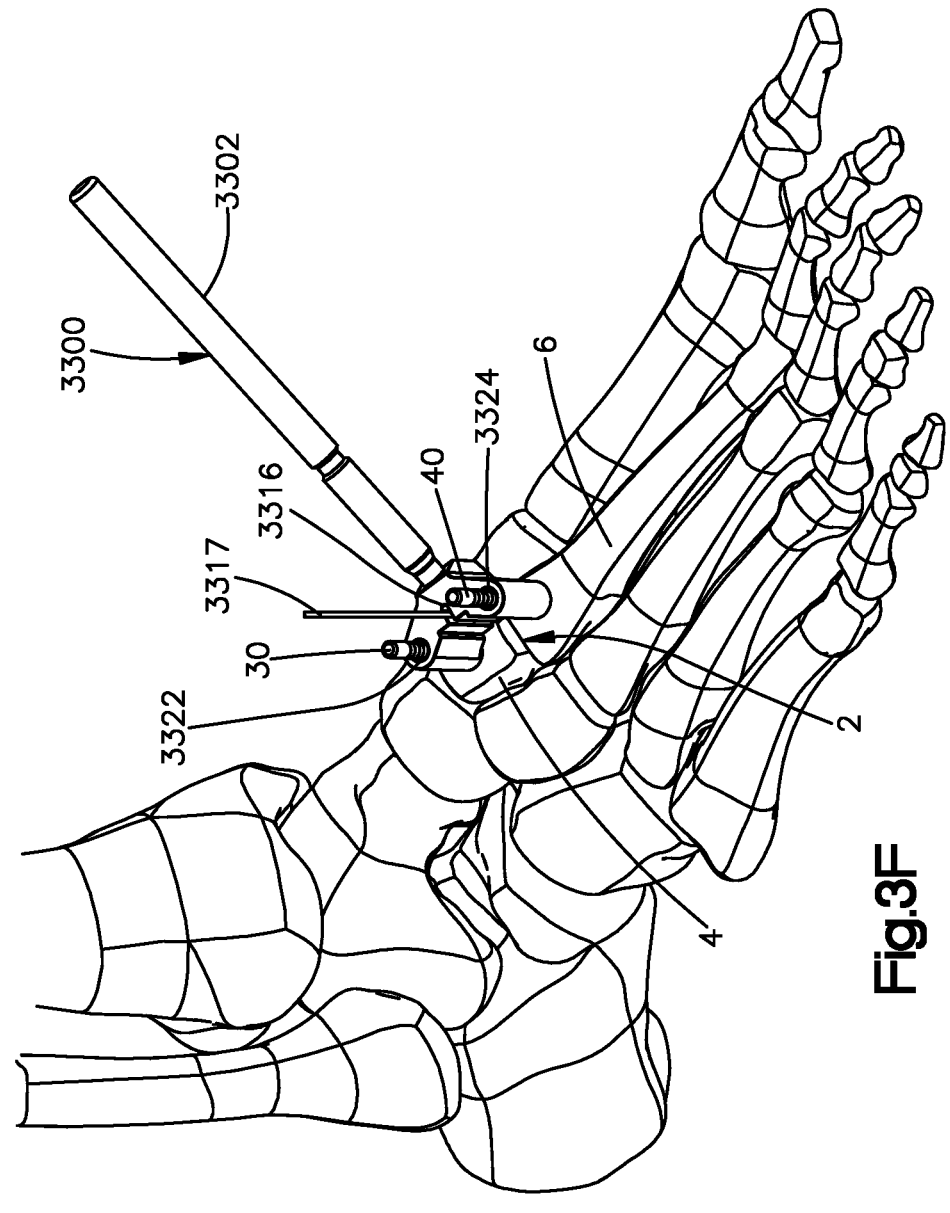
FIG. 3F is a perspective view of a second guide pin inserted into the second hole.
Figure 4:
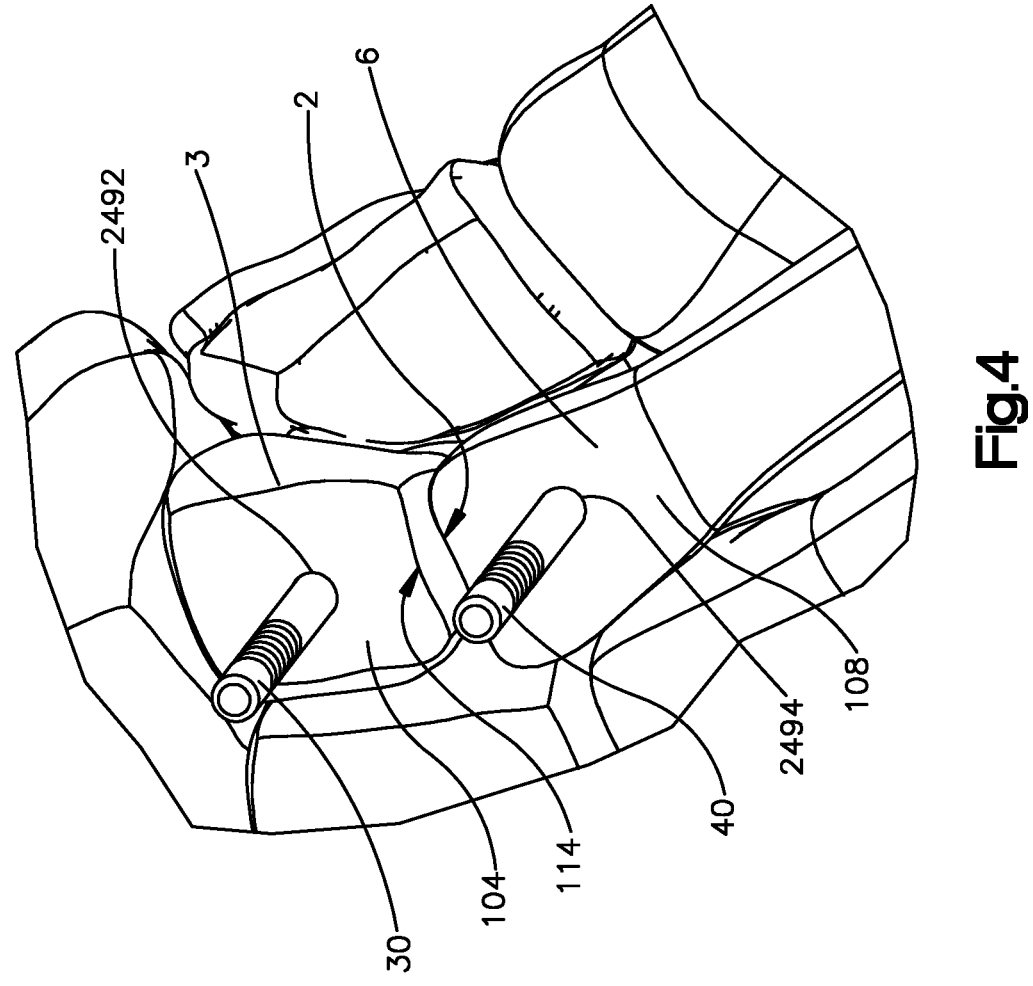
FIG. 4 is a perspective view showing the first and second guide pins inserted into the first and second bones with the drill guide removed.
Figure 5A:
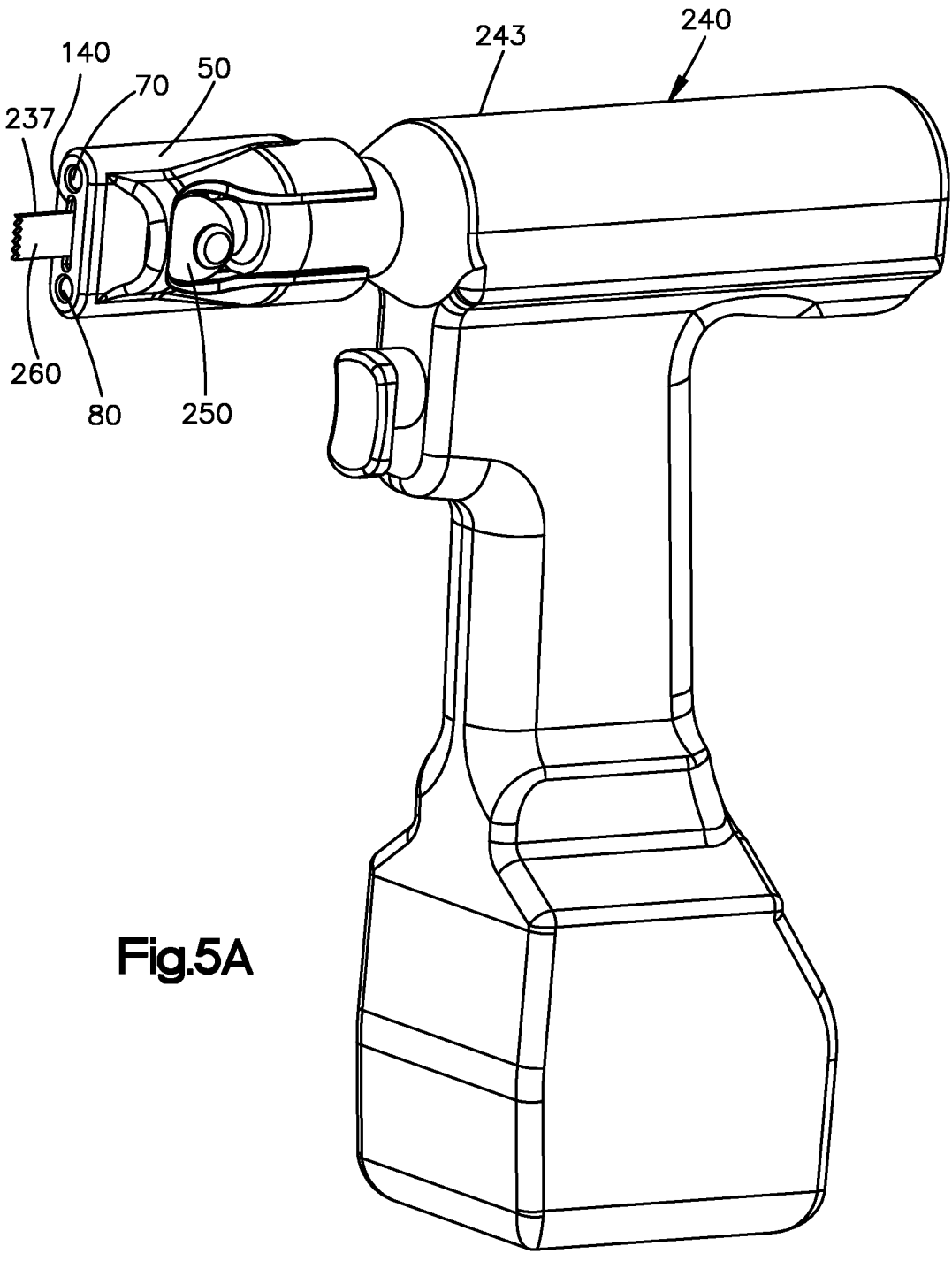
FIG. 5A is a perspective view of a surgical saw constructed in accordance with one embodiment, including a saw body, a blade attachment assembly having a saw blade, and a saw guide.
Figure 5B:
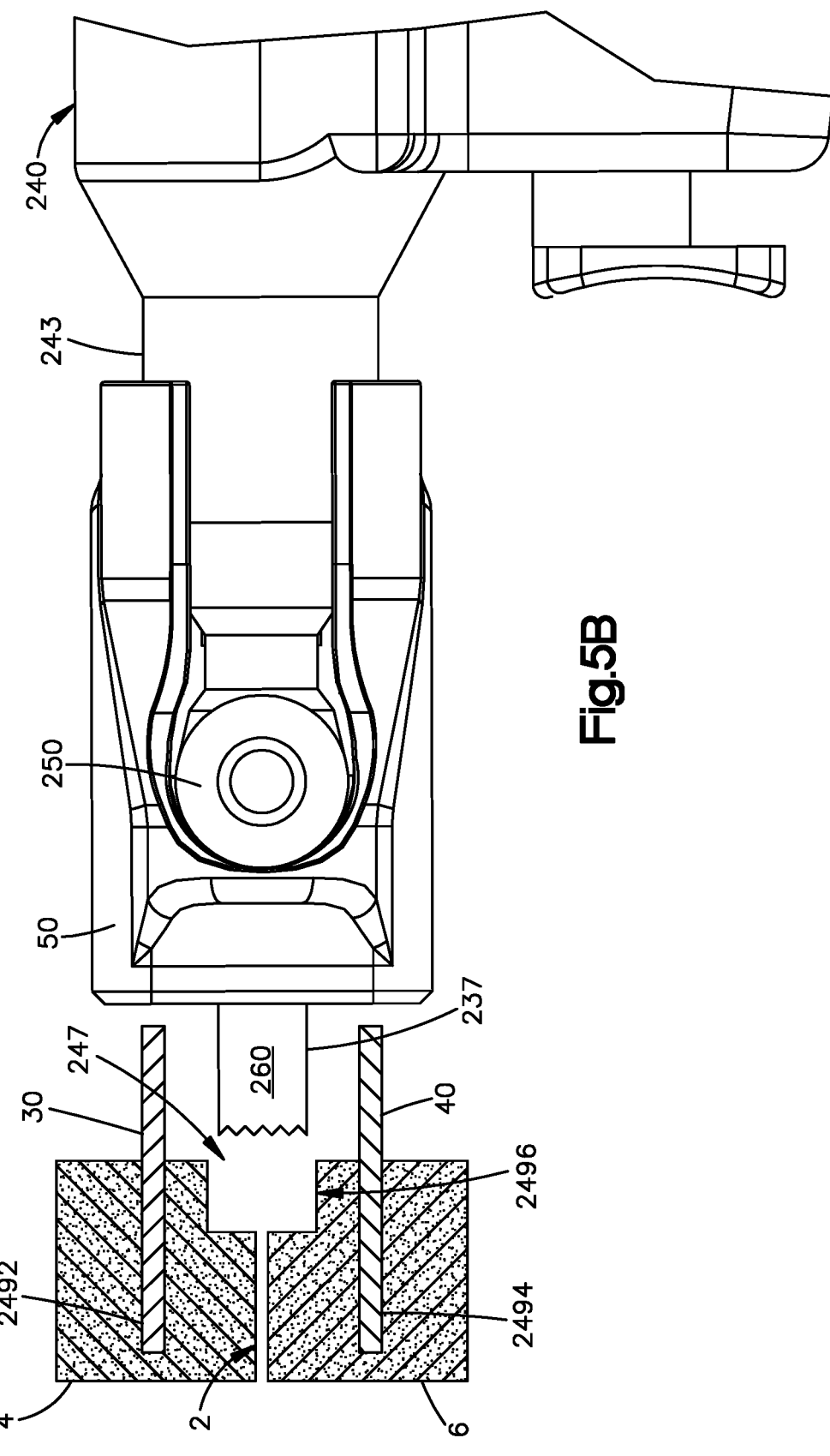
FIG. 5B is a side elevation view of the surgical saw of FIG. 5A shown after creating a middle opening in bone.
Figure 6A:
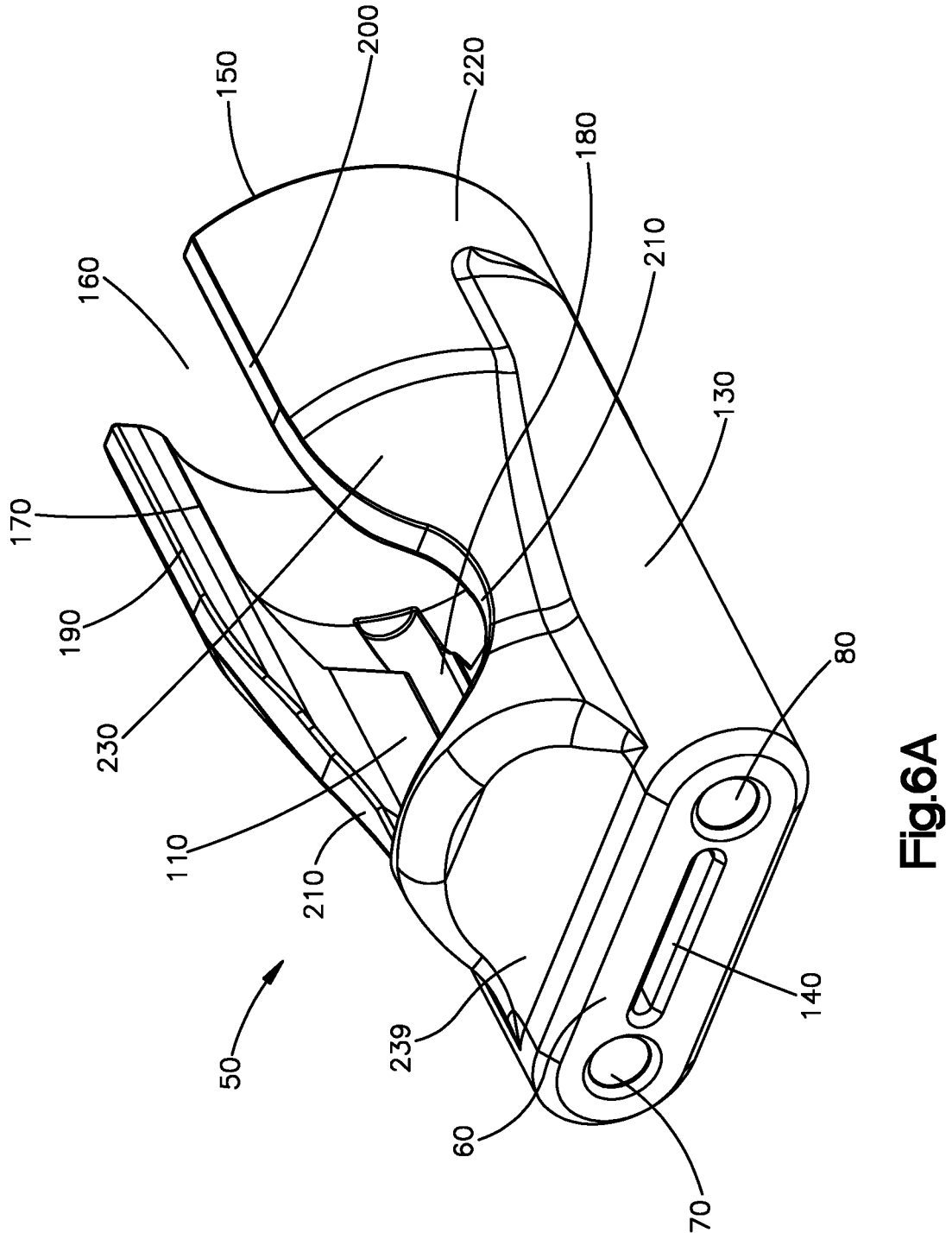
FIG. 6A is a perspective view of a saw guide.
Figure 6C:
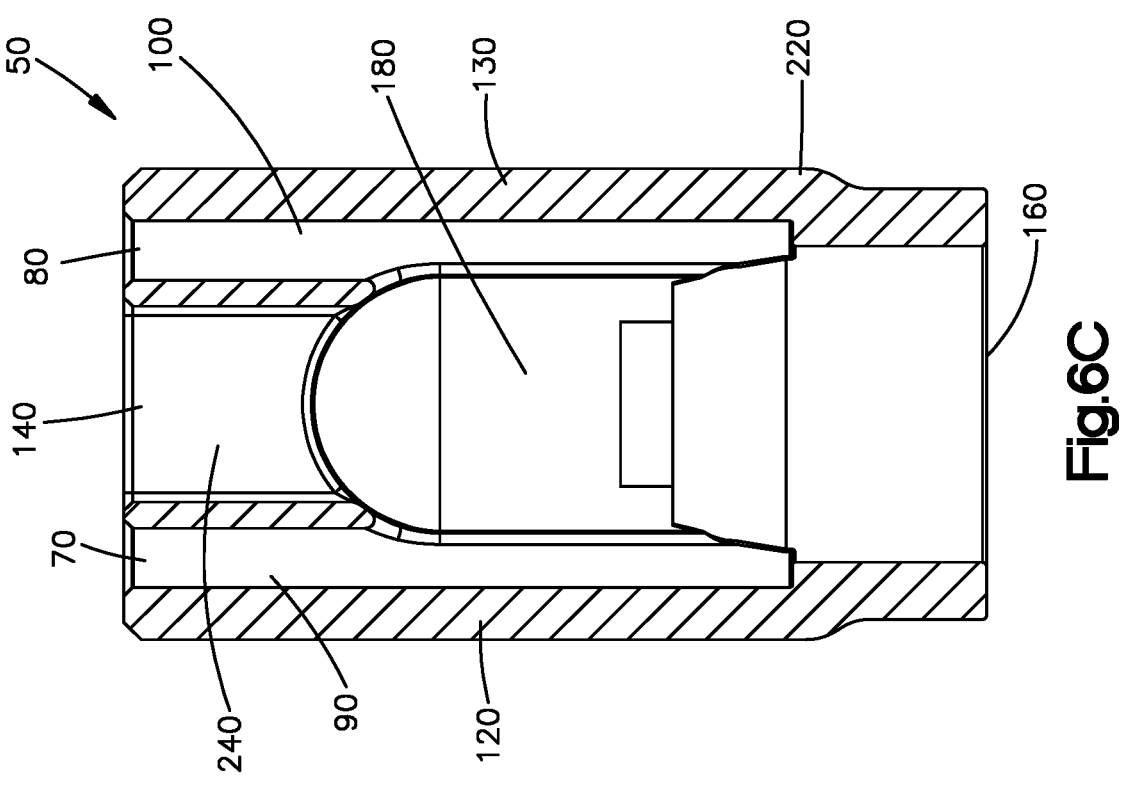
FIG. 6C is a cross-sectional view of the saw guide of FIG. 6A.
Figure 6B:
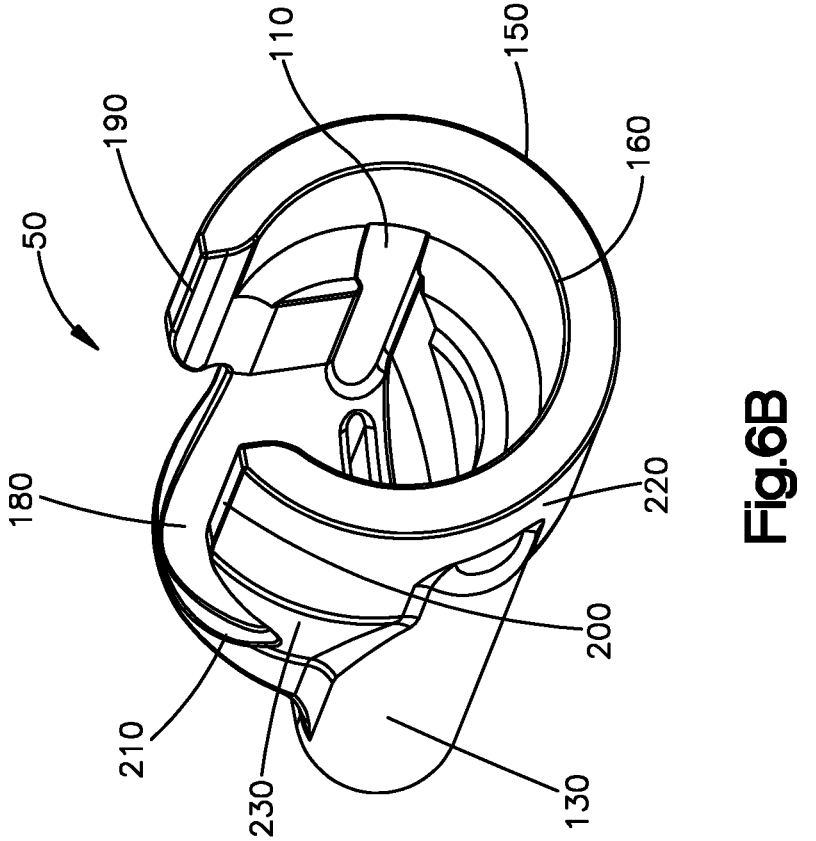
FIG. 6B is another perspective view of the saw guide of FIG. 6A.

Referring to FIGS. 3F-4, once the second hole 2494 has been created, a second or distal guide pin 40 may be inserted through second guide channel 3324 and into the second hole 2494. In particular, the drill bit 2550 can be removed from the second bone 6 and the second channel 3324. Subsequently, the second guide pin 40 can be driven through the second channel 3324 of the guide 3304 and into the second hole 2494. The second guide pin 40 can be fully inserted into an entirety of the depth of the second hole 2494. In other examples, the guide 3304 can be removed from the second bone 6 prior to inserting the second guide pin 40 into the second hole 2494. In this regard, the second guide pin 40 can be driven into the second hole 2494 without first being driven through the second guide channel 3324.

As described above, the first guide pin 30 can be inserted into the first hole 2492 prior to creating the second hole 2494. This can provide stabilization of the drill guide 3300 during drilling of the second hole 2494. Alternatively, the first and second holes 2492 and 2494 can be created in the manner described above prior to inserting the first and second guide pins 30 and 40 into the respective first and second holes 2492 and 2494. The first and second guide pins 30 and 40 can be driven through the first and second channels 3322 and 3324 of the guide 3304 and into the first and second holes 2492 and 2494, respectively. The first and second channels 3322 and 3324 can guide the first and second guide pins 30 and 40 into the first and second holes 2492 and 2494, respectively. Alternatively, the drill guide 3304 can be removed from the bones 4 and 6 prior to driving the first and second guide pins 30 and 40 into the first and second holes 2492 and 2494, respectively. Thus, the first and second guide pins 30 and 40 can be driven into the first and second holes 2492 and 2494, respectively, without first passing through the first and second channels 3322 and 3324 of the drill guide 3304. If the first and second guide pins 30 and 40 are driven through the first and second holes 2492 and 2494 and into the first and second bones 4 and 6, the drill guide assembly 3300 can be subsequently removed from the bone.

It should be appreciated that the central axes of the first and second channels 3322 and 3324 of the drill guide 3304 are substantially parallel to the orientation of the opening 3316, and thus to the orientation of the locator 3317. Because the locator 3317 is oriented substantially parallel to the joint 2, when the first and second holes 2492 and 2494 are created, the holes 2492 and 2494 similarly extend into the bones 4 and 6 along a direction substantially parallel to each other and substantially parallel to the joint 2. Accordingly, when the guide pins 30 and 40 are driven into the first and second holes 2492 and 2494, respectively, the guide pins are oriented substantially parallel to each other, and substantially parallel to the joint 2.

The drill guide assembly 3300 can be removed by gripping the handle 3302 and moving the guide 3304 away from the first and second bones 4 and 6. The locator 3317 can be removed from the joint 2 at any time after creation of the first and second holes 2492 and 2494. Thus, the locator 3317 can be removed prior to or after removal of the drill guide assembly 3300.

Referring now to FIGS. 4-6C, after insertion of the guide pins 30 and 40, a surgical cutting instrument such as a surgical saw 240 can form a third or intermediate hole 2496 into either or both of the bones 4 and 6 at a location between the first and second openings 2492 and 2494. The middle opening 2496 can be sized to receive a keel 2450 of the implant 2400 (see FIG. 9B). As will be appreciated from the description below, the surgical saw 240 can receive the first and second pins 30 and 40 to maintain the position of the pins 30 and 40, and the respective underlying bones that received the guide pins 30 and 40, at a fixed distance, thereby preventing the bones from migrating apart while the middle opening 2496 is created by a blade 260 of the saw.

In one example, the surgical saw 240 can include a saw body 243, a saw guide 50 that can be attached or otherwise supported by the saw body 243, and a blade attachment assembly 250 that can be attached or otherwise supported by the saw body. The saw guide 50 can include a distal face 60 and first and second guide holes 70 and 80 that extend through the distal face. The first and second guide holes 70 and 80 can open into respective first and second guide channels 90 and 100, respectively, that extend proximally into the saw guide 50 from the distal face 60. The blade attachment assembly 250 can support the cutting implement 237. In some examples, the cutting implement 237 can be configured as an oscillating saw blade 260. It should be appreciated that the cutting implement 237 can be alternatively configured as desired so as to create the intermediate hole 2496. The intermediate hole 2496 can be created in each of the first and second bones 4 and 6 across the joint 2. Alternatively, the intermediate hole 2496 can be created in one of the first and second bones 4 and 6 without extending into the other of the first and second bones 4 and 6.

The first and second guide holes 70 and 80 can be configured to receive the first and second guide pins 30 and 40, respectively, so as to guide the surgical saw 240, and in particular a cutting implement 237 of the saw 240 such as a blade 260, toward a target cut location 247. As will be appreciated from the description below, the target cut location 247 can be defined by the first and second bones 4 and 6 across the joint 2. Alternatively, the target cut location can be defined by only the first bone 4. Alternatively still, the target cut location can be defined by only the second bone 6.

The first and second guide holes 70 and 80 can receive the first and second guide pins 30 and 40, respectively. The first and second guide pins 30 and 40 can travel through the respective first and guide second guide holes 70 and 80 of the distal face 60. In some examples, the first and second guide pins 30 and 40 can further travel into respective portions of the first and second guide channels 90 and 100 from the first and second guide holes 70 and 80, respectively. The first and second guide holes 70 and 80 can be beveled at their distal end as desired so as to assist in insertion of the first and second guide pins 30 and 40 into the first and second guide holes 70 and 80, respectively.

The first and second guide holes 70 and 80, and can be oriented substantially parallel to each other. In particular, the first and second guide holes 70 and 80 can be oriented along a longitudinal direction that includes the proximal and distal directions. The first and second guide holes 70 and 80 can have respective diameters that are sized substantially equal to the diameters of the first and second guide pins 30 and 40. Therefore, the outer surfaces of the first and second guide pins 30 and 40 guide the surgical saw 240 such that the cutting implement 237 remains in alignment with the target cut location 247 as the surgical saw 240 is advanced toward the underlying bone. Further, the first and second guide holes 70 and 80 can be sized substantially equal to the pins 30 and 40 and can be spaced from each other a fixed distance.

Therefore, when the first and second guide holes 70 and 80 are inserted over the first and second guide pins 30 and 40, respectively, the holes 70 and 80 can receive the first and second pins 30 and 40 to maintain the position of the pins 30 and 40, and the respective underlying bones that received the guide pins 30 and 40, at a fixed distance, thereby preventing the bones from migrating apart while the middle opening 2496 is created by the blade 260 of the saw. The first and second guide channels 90 and 100 can extend proximally from the first and second guide holes 70 and 80, and thus can be spaced at the same fixed distance and can be sized to receive the first and second guide pins 30 and 40, respectively, in the event that the guide pins 30 and 40 extend fully through the first and second guide holes 70 and 80.

Referring now to FIGS. 5A-6C, the saw guide 50 can include a proximal portion 220, a distal portion 239, and an intermediate portion 230 that extends from the proximal portion 220 to the distal portion 239. A distal direction of the surgical saw 240 is thus defined from the proximal portion 220 toward the distal portion 239. Conversely, a proximal direction of the surgical saw 240 is thus defined from the distal portion 239 to the proximal portion 220. The proximal portion 220 can be a cylindrical portion having a substantially cylindrical shape, the distal portion 239 can be an oblong portion having an oblong shape, and the intermediate portion 230 can taper from the proximal portion 220 to the distal portion 239. Of course, the saw guide 50 can define any suitable size and shape as desired. The first and second guide holes 70 and 80 and the first and second guide channels 90 and 100 can be defined by the distal portion 239. In some examples, the first and second guide channels 90 and 100 can further extend into the intermediate portion 230 as desired.

In some examples, the oblong distal portion 239 has a distal bone-facing face 60 that defines first and second holes 70 and 80 to the first and second channels 90 and 100, respectively. The first and second channels 90 and 100 can be defined by any suitable structure of the guide as desired. In one example, the channels 90 and 100 can be formed as respective grooves 110 in respective opposed interior sides of the guide 50. Respective surfaces of the grooves 110 can be configured to contact the guide pins 30 and 40 if the guide pins 30 and 40 extend through the first and second guide holes 70 and 80 and into the first and second guide channels 90 and 100. In some embodiments, the saw guide 50 comprises first and second opposed lobes 120 and 130, and the first and second channels 90 and 100. Thus, the grooves 110 can be formed within the lobes 120 and 130. In some embodiments the lobes 120 and 130 can be disposed in the tapered intermediate portion 230 and the oblong distal portion 239 of the guide 50.

The distal portion 239 can further define an opening in the form of a slot 140 that extends into the distal face 60 and into the guide in the proximal direction. The slot 140 can be positioned between the first and second channels 90 and 100. The slot 140 may be sized to receive the cutting implement 237 of the surgical saw 240. In particular, the cutting implement 237 can extend distally through the slot 140. When the cutting implement 237 is configured as an oscillating blade 260, the slot 140 can have a width greater than that of the blade 260 so as to provide lateral clearance that permits oscillation of the blade 260 in the slot 140. The width can be measured along a direction perpendicular to the longitudinal direction that includes the proximal direction and the distal direction. In some embodiments, the slot 140 can define a continuous opening in the distal face 60 from the first guide hole 70 to the second guide hole 80. It should be appreciated that while the opening can be configured as a slot 140 in one example, the opening can assume any suitable size and shape as desired so as to accommodate the cutting implement 237.

The guide 50 can include a proximal opening 160 that extends into the proximal portion 220 of the guide 50. The proximal opening 160 can include a proximal opening 160 can be sized to receive a portion of the surgical saw 240. For example, the proximal opening 160 may be sized to receive at least a portion of a blade attachment assembly 250 (see FIG. 7) of the surgical saw 240. The guide 50 can additionally include a side opening defined by openings 170 and 180 into the proximal and intermediate portions 220 and 230, respectively. Thus, the opening 170 into the proximal portion 220 can define a proximal portion of the side opening. The opening 180 into the intermediate portion 230 can define a distal portion of the side opening. The openings 170 and 180 can be continuous with each other. The side opening is configured to receive a portion of the blade attachment assembly 250. In particular, the blade attachment assembly 250 can slide into the side opening in the distal direction and seat in the guide 50 at the distal end of the side opening. The proximal portion 270 of the side opening can provide a continuous opening with the proximal opening 160 of the guide 50. Further, the proximal portion 270 of the side opening can be defined by opposed edges 190 and 200. The edges 190 and 200 can be substantially straight and parallel to each other. The edges 190 and 200 can be opposite each other along a lateral direction that defines the width of the slot 140. Thus, the lateral direction can be perpendicular to the longitudinal direction. The distal portion 180 of the side opening can be defined by opposed curved edges 210. In some embodiments, the curved edges 210 may extend along respective undulating paths. The curved edges 210 can be parallel to each other. Further, the curved edges 210 can curve a transverse direction that is perpendicular to each of the lateral direction and the longitudinal direction.

Figure 7:
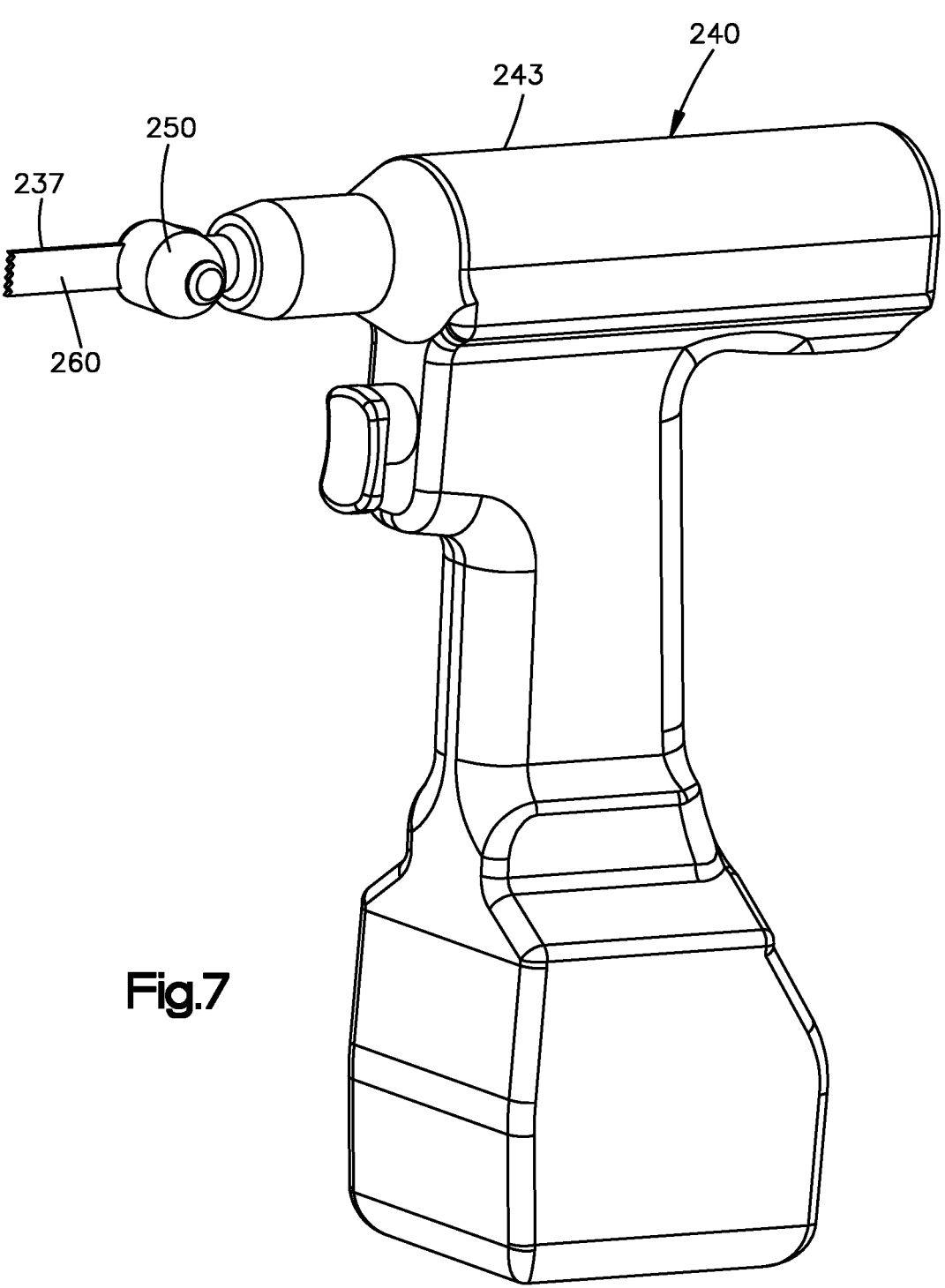
FIG. 7 is a perspective view of a surgical saw including the blade attachment assembly.

Referring now also to FIG. 7, the surgical saw 240 is shown with the saw guide removed so as to better illustrate the saw blade attachment assembly 250 that is attached to the saw body 243. The saw blade attachment assembly 250 can further be attached to the guide 50 in the manner described above. The saw blade attachment assembly 250 can include the saw blade 260. During attachment of the saw guide 50, the blade attachment assembly 250 with attached saw blade 260 is inserted into the proximal opening 150 of the saw guide 50. The blade attachment assembly 250 slides through the proximal portion 170 of the side opening in the saw guide 50 and can seat against the saw guide 50 at the distal end of the distal portion 180 of the side opening. The curved edges 210 of the side opening 180 can partially encircle a curved portion of the blade attachment assembly 250. The saw blade 260 extends through the slot 140 in the saw guide 50 in the distal direction.

During operation, referring again to FIG. 5B, the saw guide 50 is attached to the surgical saw 240 in the manner described above. Next, the saw guide 50 is positioned such that the first and second guide holes 70 and 80 are aligned with the first and second guide pins 30 and 40, respectively, that have been inserted into the first and second bones 4 and 6 in the manner described above. When the first and second guide pins 30 and 40 are received by the first and second guide holes 70 and 80, the cutting implement 237 is aligned with each of the first and second bones 4 and 6 across the joint 2. The surgical saw 240 is then advanced in the distal direction guided by the first and second guide pins 30 and 40 until the cutting implement 237 contacts the underlying first and second bone 4 and 6 across the joint. Cutting movement of the cutting implement 237 (which can be an oscillation in the case of a saw blade, or rotation in the case of a drill bit), causes the cutting instrument to create the third or intermediate hole 2496 in the first and second bones 4 and 6 across the joint 2. When the cutting implement 237 is configured as the oscillating blade 260, the third or intermediate hole 2496 can be a slot that is elongate along a direction between the first and second holes 2492 and 2494. The slot can have a rectangular cross section along a direction perpendicular to the central axes of the first and second holes 2492 and 2494, or can be alternatively shaped as desired. The depth of the third or intermediate hole 2496 can be suitable to receive a keel 2450 of the implant 2400 (see FIG. 7B). In other embodiments, the saw guide 50 may be first slid over the temporary guide pins 30 and 40 and then coupled to the saw 240 to form the third or intermediate hole 2496. The first and second holes 70 and 80 can receive the first and second guide pins 30 and 40, respectively, in the manner described above.

Figure 8:
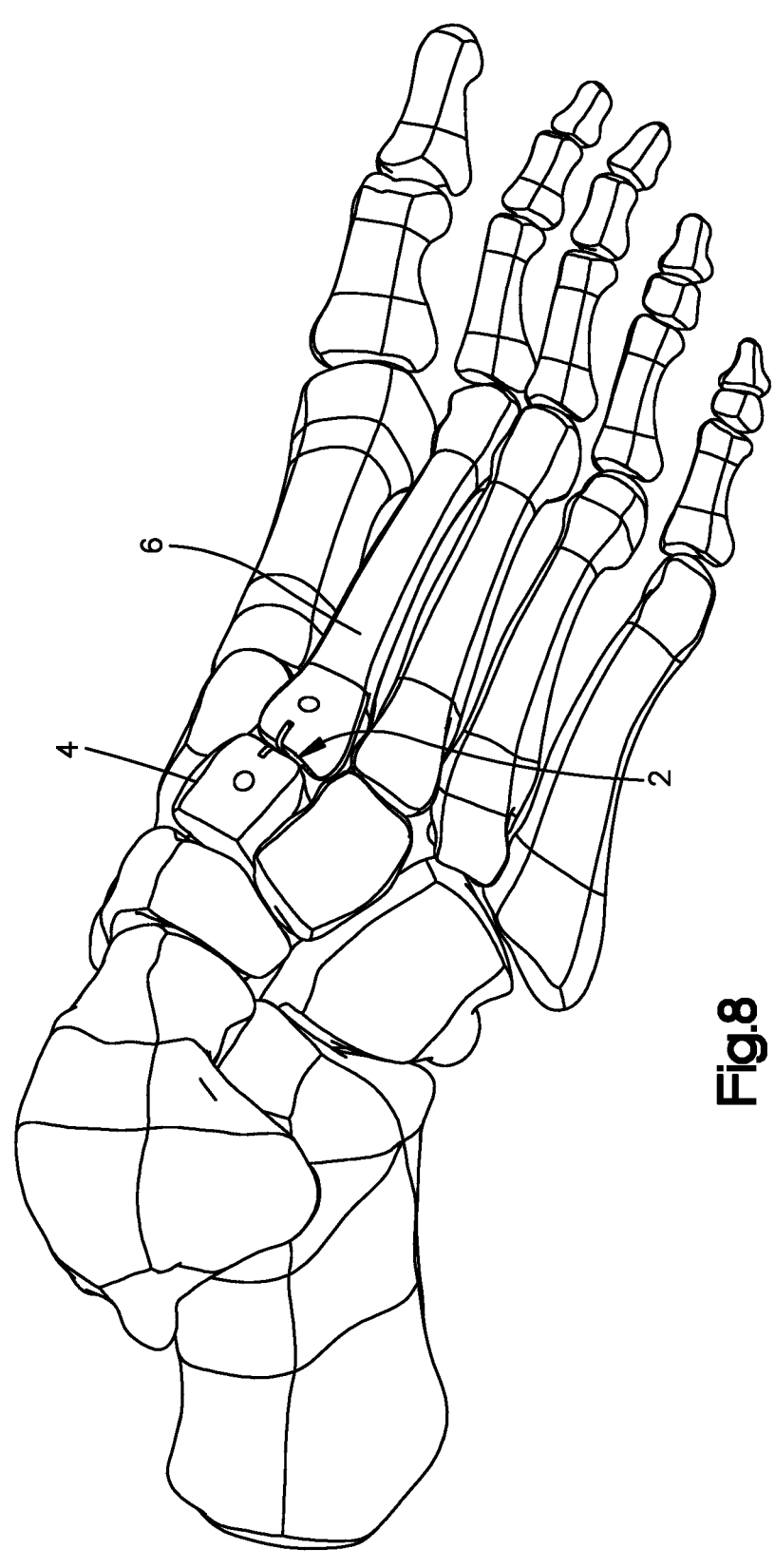
FIG. 8 is a perspective view of a human foot having the first and second holes and an intermediate hole formed in first and second bones of the foot.

Referring now also to FIG. 8, once the third or intermediate hole 2496 has been created, the surgical saw 240 can be removed from the guide pins 30 and 40 along the proximal direction, thereby exposing the third or intermediate hole 2496. The first and second guide pins 30 and 40 can be removed to expose the first and second holes 2492 and 2494. The holes 2492, 2494, and 2496 can then be configured to receive the implant 2400. Because the first and second guide pins 30 and 40 are removed prior to completion of the surgical procedure, the first and second guide pins 30 and 40 can be referred to as temporary guide pins. This is distinguished from a permanent implant that is designed to remain implanted after completion of the surgical procedure. In this regard, it should be appreciated that the first and second holes 2492 and 2494 can receive respective temporary guide members in the form of the guide pins 30 and 40 that guide the movement of the surgical saw 240 to create the third or intermediate hole 2496, and the same first and second holes 2492 and 2494 can then receive a permanent implant to provide fixation across the joint 2.

While the first and second guide pins 30 and 40 can guide the cutting implement 237 to the first and second bones 4 and 6 across the joint 2 in the manner described above, it should be appreciated that the first and second guide pins 30 and 40 can alternatively be positioned so as to guide the cutting implement 237 to the first bone 4 and not the second bone 6. Alternatively still, the first and second guide pins 30 and 40 can be positioned so as to guide the cutting implement 237 to the second bone 6 and not the first bone 4.

Figure 9A:
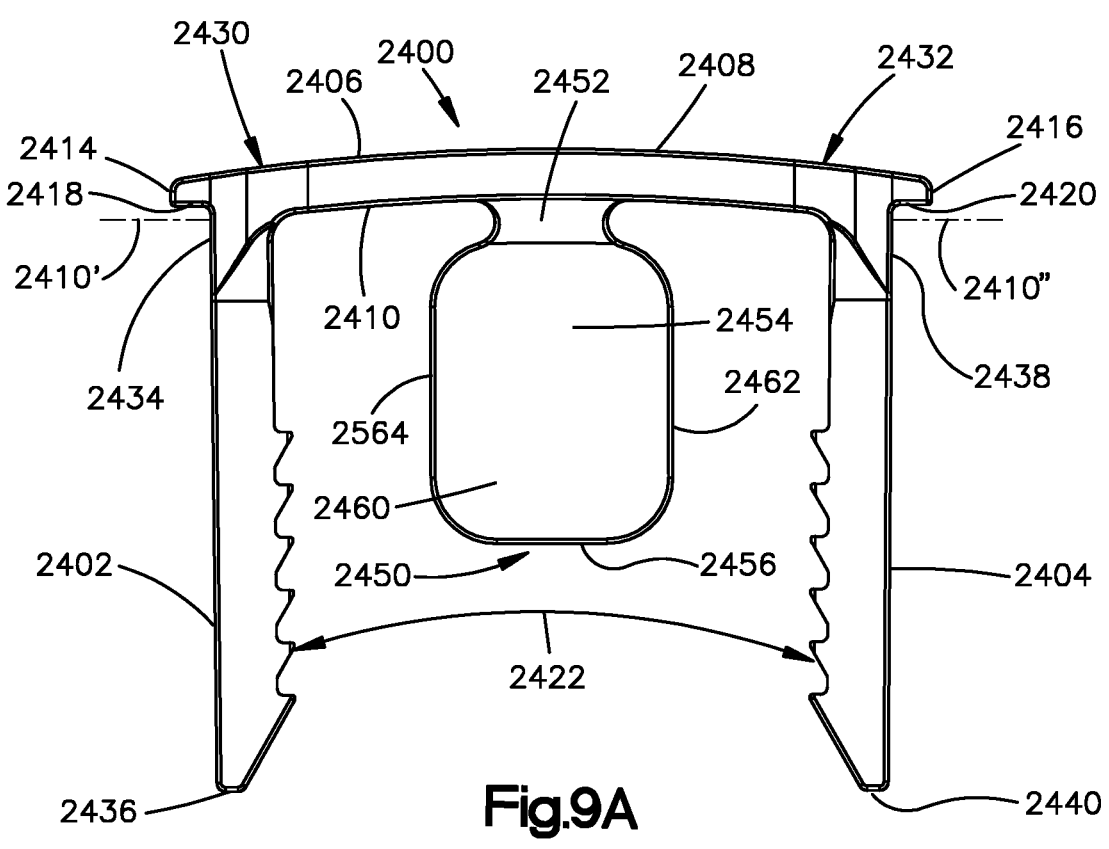
FIG. 9A is a side view of a bone fixation clip.
Figure 9B:
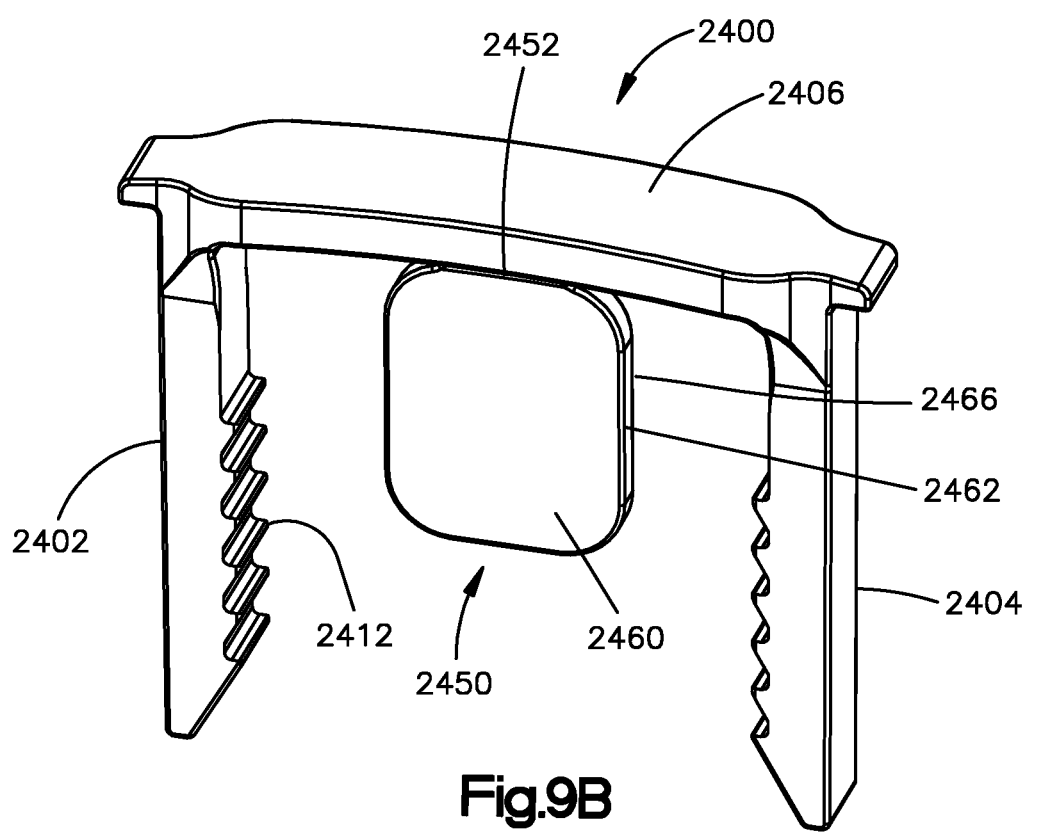
FIG. 9B is a perspective view of a bone fixation clip.

Referring now to FIGS. 9A-9B, a bone implant 2400 for insertion of the holes 2492, 2494, and 2946 (see FIG. 8) can be configured as a clip having a bridge 2406 and first and second bone engaging legs 2402 and 2404 that extend out from the bridge 2406. The bridge 2406 can be said to extend along a longitudinal direction, which can be straight or curved. As will be appreciated from the description below, the first and second legs 2402 and 2404 can be bone engagement members that are configured to be inserted into respective holes that extend into bone. The bone implant 2400 can further include an anti-torque keel 2450 that extends from the bridge 2406 at a location between the legs 2402 and 2404. For instance, the anti-torque keel 2450 can be equidistantly spaced from the legs 2402 and 2404 in some examples. As will be appreciated from the description below, the keel 2450 can provide stability to the bones and can resist rotation and shear forces acting on bones, and can further provide stabilization of the bone implant 2400 against rotation. The anti-torque keel 2450 can also be referred to as a tab, keep, post, or implant. One or more clips 2400 may be implanted as described below in a single procedure, for instance to joint two bones together.

The first and second legs 2402 and 2404, and the keel 2450 can all be monolithic with each other so as to define a unitary clip body. The bridge can be monolithic with the clip body, or can be separate from and attached to the clip body as desired. In other embodiments within the scope of the disclosure, a clip may include more than two bone engaging members; or alternatively may include openings for one or more independent fasteners in lieu of the bone engaging members. In other embodiments of the disclosure, the implant 2400 may be more similar to a plate. The implant can alternatively be constructed as described in U.S. Pat. No. 11,179,149, the disclosure of which is hereby incorporated by reference as if set forth in its entirety herein.

The first leg 2402 extends from a first end 2430 of the bridge 2406 and the second leg 2404 can extend from an opposite second end 2432 of the bridge 2406. The first leg 2402 has a first proximal end 2434 that extends from the first end 2430, and a first distal end 2436 opposite the first proximal end 2434 in a distal direction. Conversely, the first proximal end 2434 is opposite the first distal end 2436 in a proximal direction that is opposite the distal direction The second leg 2404 has a second proximal end 2438 that extends to the second end 2432 of the bridge 2406, and a second distal end 2440 that is opposite the second proximal end 2338 in the distal direction. Conversely, the second proximal end 2438 is opposite the second distal end 2440 in the proximal direction. The first and second distal ends 2346 and 2440 can be free terminal ends of the first and second legs 2402 and 2404, respectively.

The bridge 2406 has at least one proximal or outer surface 2408 and at least one distal or inner surface 2410 that is opposite the outer surface 2408 in the distal direction. The inner surface 2410 can be referred to as a bone facing surface. The first and second legs 2402 and 2404 extend from the inner surface 2410. The first and second legs 2402 and 2404 can have surface features 2412 that may improve bone purchase or improve pull out strength of the implant 2400 from bone. The surface features 2412 can be referred to as teeth or serrations. The surface features 2412 can be disposed on respective sides of the legs 2402 and 2404 that face each other, but can be on any or all sides of the legs.

The bone implant 2400 may have first and second shoulders 2414 and 2416 or other connecting structure configured to be connected with an inserter. The first and second shoulders 2414 and 2416 may also be referred to as tabs, ears, protrusions, wings, retainers, or retaining members. The first shoulder 2414 can extend outward from the first end 2430 of the bridge 2406 along the longitudinal direction, and the second shoulder 2416 can extend outward from the second end 2432 of the bridge 2406 along the longitudinal direction. In other examples, the shoulders 2414 and 2416 can extend out from the bridge 2406 along a direction that is angularly offset, for instance perpendicular, to the longitudinal direction. The first and second shoulders 2414 and 2416 can have respective first and second inner surfaces 2418 and 2420 that define bone-facing surfaces. The inner surfaces 2418 and 2420 can releasably engage with an inserter, which can allow the implant to be side loaded, top loaded, or pivotably loaded. In some examples, the first and second inner surfaces 2418 and 2420 can be offset with respect to the inner surface 2410 of the bridge 2406 in the proximal direction. The dashed extension lines 2410' and 2410" show the level of the inner surface 2410 versus the first and second inner surfaces 2418 and 2420.

The anti-torque keel 2450 extends in the distal direction from the inner surface 2410 of bridge 2406. In one example, a single keel 2450 is centered between the legs 2402 and 2404. In other examples, the keel 2450 can be off-center relative to the legs 2402 and 2404, and/or the implant 2400 can include a plurality of keels. The keel 2450 can also be connected to the implant body at more than one location along the inner surface 2410 of the bridge 2406. The keel 2450 can include a neck portion 242 that extends from the bridge 2406, a body 2454 that extends from the next portion 2452 in the distal direction, and a tip 2456 that defines a free distal end of the keel 2450. The keel 2450 can be rectangular in cross-section and includes four sides 2460, 2462, 2464, and 2466. The keel 2450 defines a thickness between sides 2460 and 2466 that can be less than, the same as, similar to, or greater than the thickness of the bridge 2406 and/or the legs 2402 and 2404 in the same direction (front-back). The keel thickness between the sides 2460 and 2466 is less than the thickness of the bridge 2406 and legs 2402 and 2404 in the same direction. The keel 2450 does not prevent compression of the bones by the legs 2402 and 2404, at least because the keel is oriented in a plane coplanar with, or parallel to, the plane of the bridge 2406 and legs 2402 and 2404.

In some examples, the bone implant 2400 is formed of an elastic material, such as nitinol, which permits the clip to be deformed into the configuration shown in FIGS. 9A and 9B, where the legs 2402 and 2404 are substantially parallel. Upon insertion, the deformation may be relaxed, allowing the legs 2402 and 2404 to urge towards each other. This allows the bone implant 2400 to provide compression between the two bones or bone fragments, while the keel 2450 prevents rotation of the bone implant 2400.

As will be described in more detail below, an inserter can maintain the bone implant 2400 in a first configuration thereby allowing a second configuration once an inserter is disassembled from the implant. The first configuration may be an elastically deformed state, for example an insertion state. The second configuration may be a free state or an implanted state, as seen in FIG. 9A, such that when no external forces are acting upon the bone implant 2400, other than gravity, the bone implant 2400 experiences no elastic or plastic deflection or deformation. In the free state, the legs 2402 and 2404 can converge as they extend away from the bridge 2406. Thus, the first and second distal ends 2436 and 2440 are closer together than are the first and second proximal ends 2434 and 2438. An angle 2422 is formed between the converging legs 2402 and 2404 in the free state. The angle 2422 opens toward the bridge 2406. The angle 2422 may be referred to as a free state angle.

The bone implant 2400 may be formed of an elastic material, such as nitinol, and inserted in a stressed state that is allowed to relax after insertion. This causes the legs 2402 and 2404 to urge towards each other after insertion into the first and second holes 2492 and 2494, thereby providing a compressive force to the first 4 and second 6 bones or bone fragments across the joint 2.

Referring now also to FIGS. 10A-11C, the bone implant 2400 can be inserted into underlying bone using an inserter 2700. As will now be described, the inserter is configured to selectively deform the bone implant 2400 into a stressed state, so that the legs 2402 and 2404 are urged toward each other after they are inserted into the underlying bone, and the inserter is released from the implant 2400.

The inserter 2700 may include a body 2702, a ram 2704, a ram pin 2706, a knob 2708, a shaft 2710, and a knob pin 2712. The ram 2702 and the ram pin 2706 may be coupled together as a ram sub-assembly 2714. The knob 2708, the shaft 2710, and the knob pin 2712 may be coupled together as a shaft sub-assembly 2716.

The body 2702 extends between a distal end 2718 and a proximal end 2720. The body 2702 may be a generally plate-like part that is wider at the distal end 2718 and narrower at the proximal end 2720. The distal-most aspect of the body 2702 may include two jaws or hooks 2722, 2724 that face each other across a shallow alcove 2726. The hooks 2722, 2724 include proximal surfaces 2728, 2730, respectively. The hook 2722 includes a front wall 2732 and the hook 2724 includes a back wall 2734. A notch 2736 extends proximally from a central portion of the alcove 2726. A first slot 2738 extends through the body 2702 proximal to the notch 2736 along a front-back direction. The slot 2738 is elongate along a proximal-distal direction. A second slot 2740 extends through the body 2702 proximal to the slot 2738 along the front-back direction. The slot 2740 is elongate along the proximal-distal direction. The second slot 2740 is longer than the first slot 2738 in the proximal-distal direction and is wider than the first slot 2738 in the left-right direction. A first central longitudinal hole 2742 extends proximally into the body 2702 from the distal end 2718 to the slot 2740. The slot 2738 and the hole 2742 intersect at right angles. A second central longitudinal hole 2744 extends distally into the body 2702 from the proximal end 2720 to the slot 2740. The hole 2744 may be internally threaded. The body 2702 may be thickened in the vicinity of the hole 2744 so as to adequately support the hole 2744 under expected loads.

The ram 2704 extends between a distal end 2750 and a proximal end 2752. The ram 2704 includes a distal head 2754, which may be generally rectangular as shown. As seen best in FIGS. 10A and 10C, the distal-most aspect of the head 2754 may be convex in a front or back view. A shaft 2756 extends proximally from the head 2754. The shaft 2756 may have a circular cross section as shown. The outer diameter of the shaft 2756 may be similar to the thickness of the head 2754 in a front-back direction, and may be less than the width of the head in a left-right direction. A transverse hole 2758 extends through the shaft 2756 near the proximal end 2752.

The ram 2702 and the ram pin 2706 may be coupled together to form the ram sub-assembly 2714 by inserting the ram pin through the hole 2758.

The knob 2708 may be a generally rectangular part which may be contoured to match the proximal end 2720 of the body 2702. A central longitudinal hole 2760 may extend through the knob in a proximal-distal direction. A transverse hole 2762 may extend through the knob in a front-back direction.

The shaft 2710 extends between a distal end 2770 and a proximal end 2772. The shaft 2710 may include three portions or segments along its distal-proximal length. A first portion 2774 extends proximally from the distal end 2770, has a circular cross section, and a smooth outer surface. A second portion 2778 extends proximally from the first portion 2774 and has external threads 2780. The minor diameter of the external threads may be greater than the outer diameter of the first portion 2774. A third portion 2782 extends proximally from the second portion 2778 to the proximal end 2720, has a circular cross section, and a smooth outer surface. The outer diameter of the third portion 2782 may be similar to the minor diameter of the external threads 2780. A transverse hole 2784 extends through the third portion 2782 near the proximal end 2772.

The knob 2708, the shaft 2710, and the knob pin 2712 may be coupled together to form the shaft subassembly 2716 by inserting the third portion 2782 of the shaft 2710 into the hole 2760 of the knob 2708, aligning the transverse holes 2762, 2784, and inserting the knob pin 2712 through the holes 2762, 2784.

The inserter 2700 may be assembled by inserting the shaft 2756 of the ram 2704 into the hole 2742 of the body 2702, aligning the transverse hole 2758 with the first slot 2738, and

Figures 10C, 10D:
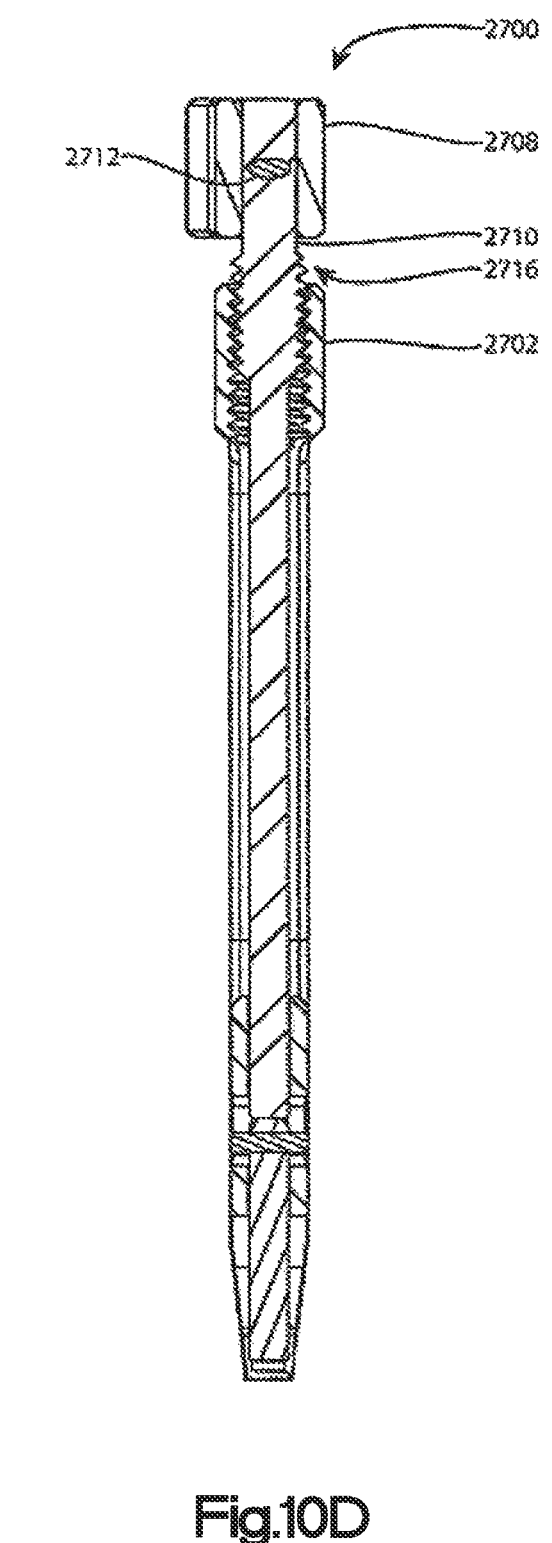
FIG. 10C is a front cross-sectional view of the implant inserter of FIG. 10A.
FIG. 10D is a side cross-sectional view of the implant inserter of FIG. 10A.
Figures 10E, 10F:
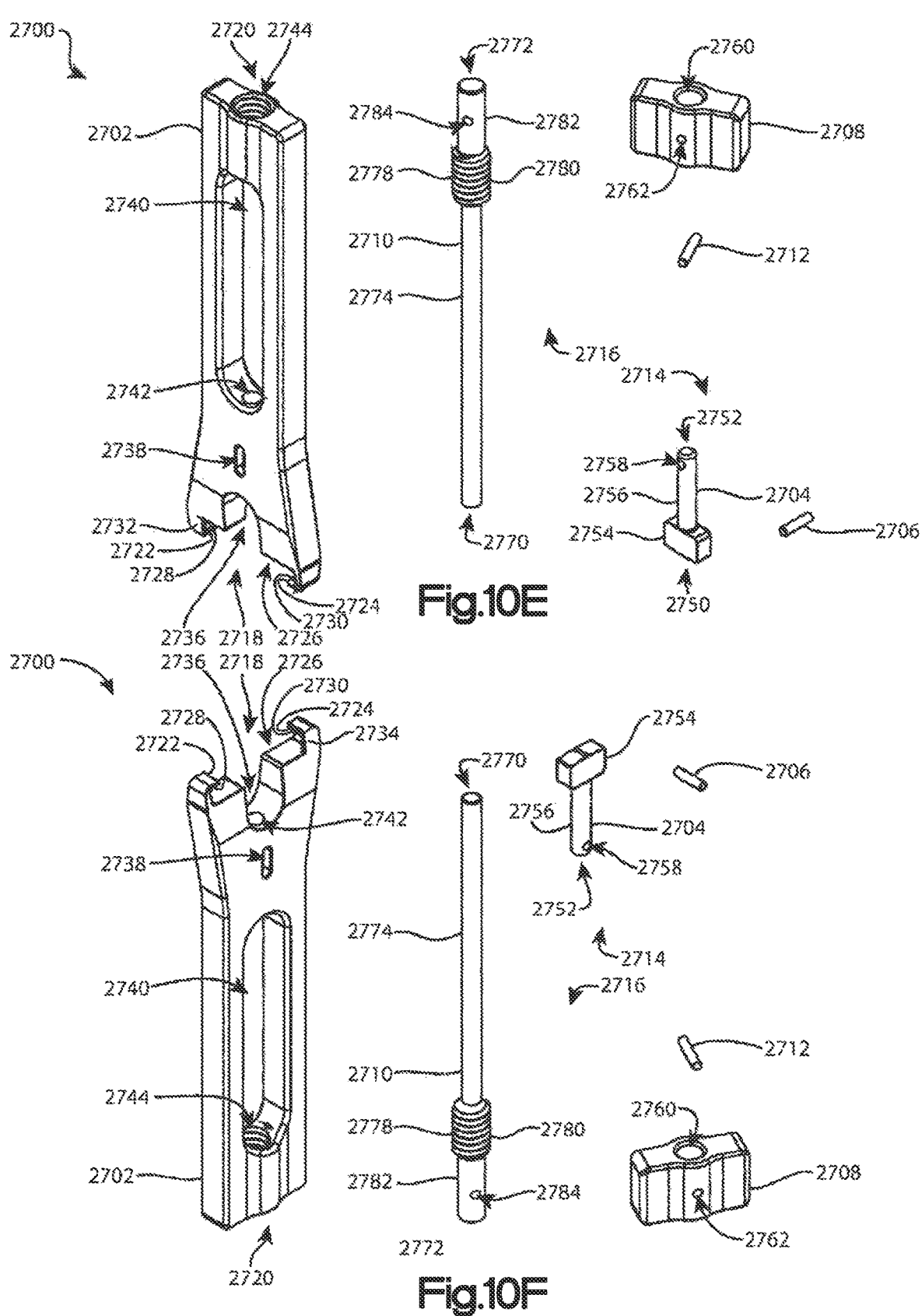
FIG. 10E is an exploded perspective view of the implant inserter of FIG. 10A.
FIG. 10F is another exploded perspective view of the implant inserter of FIG. 10E.

14 inserting the ram pin 2706 through the slot 2738 and hole 2758; and by inserting the first portion 2774 of the shaft 2710 into the hole 2744 of the body 2702 and advancing the shaft distally relative to the body until the first portion enters the hole 2742 and the external threads 2780 engage the internal threads of the hole 2744. The head 2754 may be at least partially received in the notch 2736. Referring to FIGS. 10C and 10D, the distal end 2770 of the shaft 2710 directly contacts the proximal end 2752 of the ram 2704, but the two parts are not otherwise mechanically connected.

When the inserter 2700 is operatively assembled, the ram 2704 is free to translate proximal-distal relative to the body 2702 within the constraint provided by the ram pin 2706 in the slot 2738, but the ram is prevented from rotating about its shaft 2756 relative to the body by the ram pin in the slot. The shaft sub-assembly 2716 engages the body 2702 via the external threads 2780 engaged with the internal threads of the hole 2744. Thus the shaft sub-assembly rotates and translates simultaneously relative to the body. The shaft sub-assembly 2716 is removable from the assembled body 2702, ram 2704, and ram pin 2706, which is advantageous at least for cleaning. Turning the knob 2708 clockwise advances the shaft sub-assembly 2716 distally, which pushes the ram sub-assembly 2714 distally. Turning the knob 2708 counterclockwise moves the shaft sub-assembly proximally, which permits the ram sub-assembly to move proximally under an external force such as the elastic force of a clip bridge or the force of gravity. However, the distal end 2770 of the shaft 2710 is not mechanically coupled to the proximal end 2752 of the ram 2704 in a way that enables the shaft sub-assembly 2716 to pull the ram sub-assembly 2714 proximally. It should be appreciated that the inserter 2700 can be alternatively constructed as desired.

The inserter 2700 may be coupled to the implant 2400 will be used as an example. A method of coupling the inserter 2700 to the clip 2400 may include any or all of the following steps in any order: rotating the knob 2708 counterclockwise; rotating the shaft 2710 counterclockwise; rotating the shaft sub-assembly 2714 clockwise; moving the ram 2704 proximally; moving the ram sub-assembly 2714 proximally; positioning the upper surface 2408 of the bridge 2406 of the clip 2400 against the distal-most aspect of the ram 2704; orienting the bridge 2406 relative to the body 2702 so that the front wall 2732 is in front of the connecting means 2414 and the back wall 2734 is in back of the connecting means 2416; orienting the bridge 2406 relative to the body 2702 so that the longitudinal direction established by the bridge is oblique to the left-right direction between the hooks 2722, 2724; rotating the body 2702 clockwise; sliding the hooks 2722, 2724 under the connecting means 2414, 2416; rotating the knob 2708 clockwise; rotating the shaft 2710 clockwise; rotating the shaft sub-assembly 2714 clockwise; moving the ram 2704 distally relative to the body 2702; moving the ram sub-assembly 2714 distally relative to the body 2702; and contacting the upper surface 2408 of the bridge 2406 of the clip 2400 with the distal-most aspect of the ram 2704. The inserter 2700 may be disconnected from the implant 2400 at least by reversing the assembly steps.

When the implant 2400 and the inserter 2700 are operatively assembled, the inserter 2700 may be actuated to move the implant 2400 between the free state and an elastically deformed state. Referring to FIG. 10C, clockwise rotation of the knob 2708, the shaft 2710, or the shaft sub-assembly 2716 causes the ram 2704 or the ram subassembly 2714 to move distally relative to the body 2702 against the static resistance or support of the hooks 2722, 2724 or other static support feature(s). This causes the bridge 2406 to elastically deform in three or four point bending, which causes the first and second legs 2402, 2404 to spread apart. Counterclockwise rotation of the knob 2708, the shaft 2710, or the shaft sub-assembly 2716 causes the ram 2704 or the ram sub-assembly 2714 to move proximally relative to the body 2702, reducing the proximal force of the hooks 2722, 2724 on the connecting means 2414, 2416. This allows the implant 2400 to relax and urge the legs of the implant 2400 toward the free state, thereby compressing the first and second bones 4 and 6 across the joint 2 in the manner described above (see FIG. 12B).

Figures 11A, 11B, 11C:
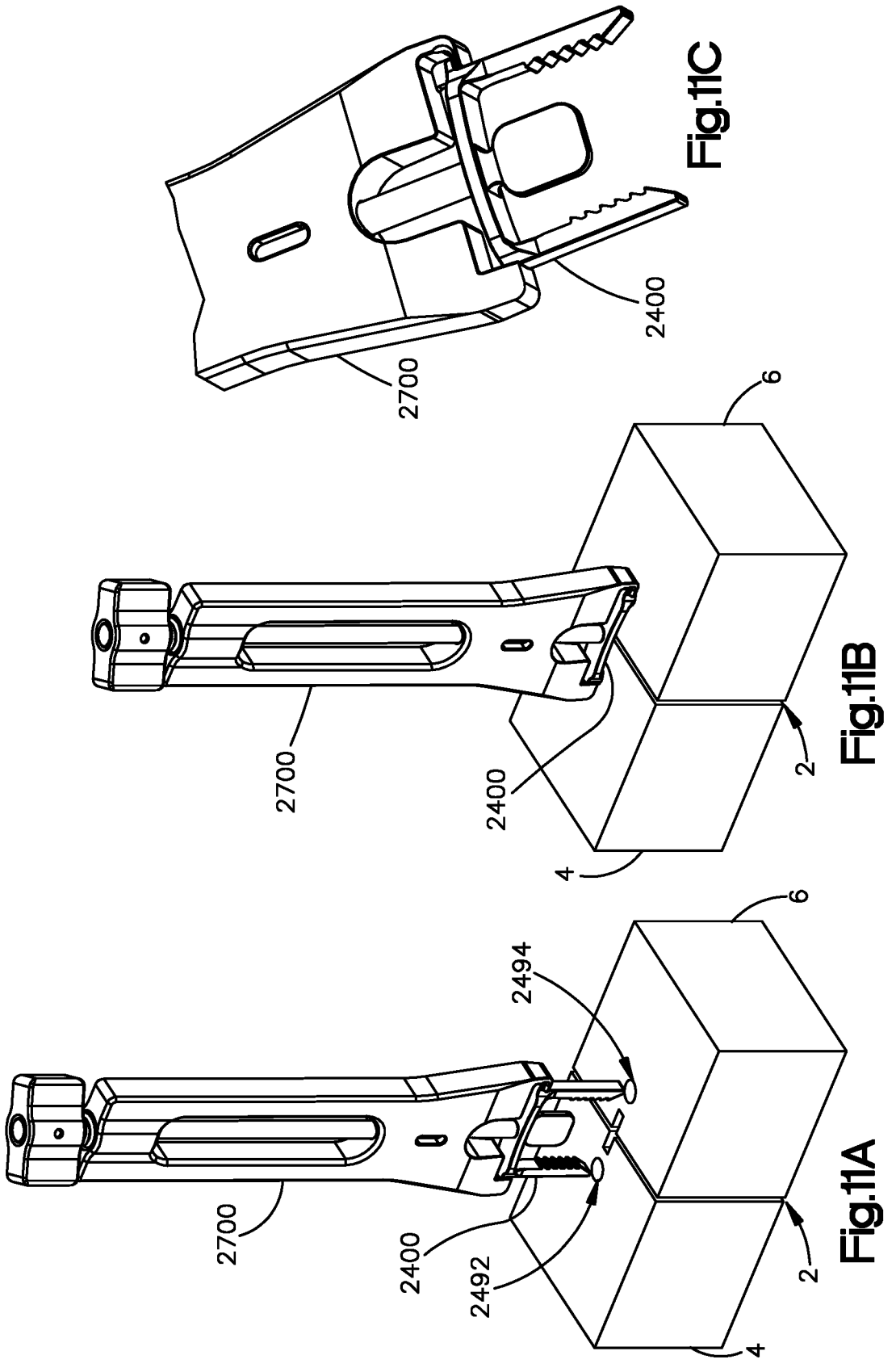
FIG. 11A is a perspective view of a clip inserter being used to insert a bone fixation clip into bone.
FIG. 11B is another perspective view of the clip inserter.
FIG. 11C is a perspective view of a clip inserter holding a bone fixation clip.

FIG. 11A shows the steps of assembling the implant 2400 and the inserter 2400; actuating the inserter 2400; moving the ram 2704 or the ram sub-assembly 2714 distally relative to the body 2702; moving the implant 2400 from the free state to an elastically deformed state; moving the first and second legs 2402 and 2404 from a distally-converging state to a parallel state; inserting the left bone engaging member 2402 in the first hole 2492; and inserting the right bone engaging member 2404 in the second hole 2494. FIG. 11B shows the steps of inserting the plug 2450 in the third hole 2496; and seating the lower surface 2410 against a surface of the first or second bone fragment. FIG. 11C is an oblique detail view of the distal end of the inserter 2700 coupled to the implant 2400.

Figure 12A:
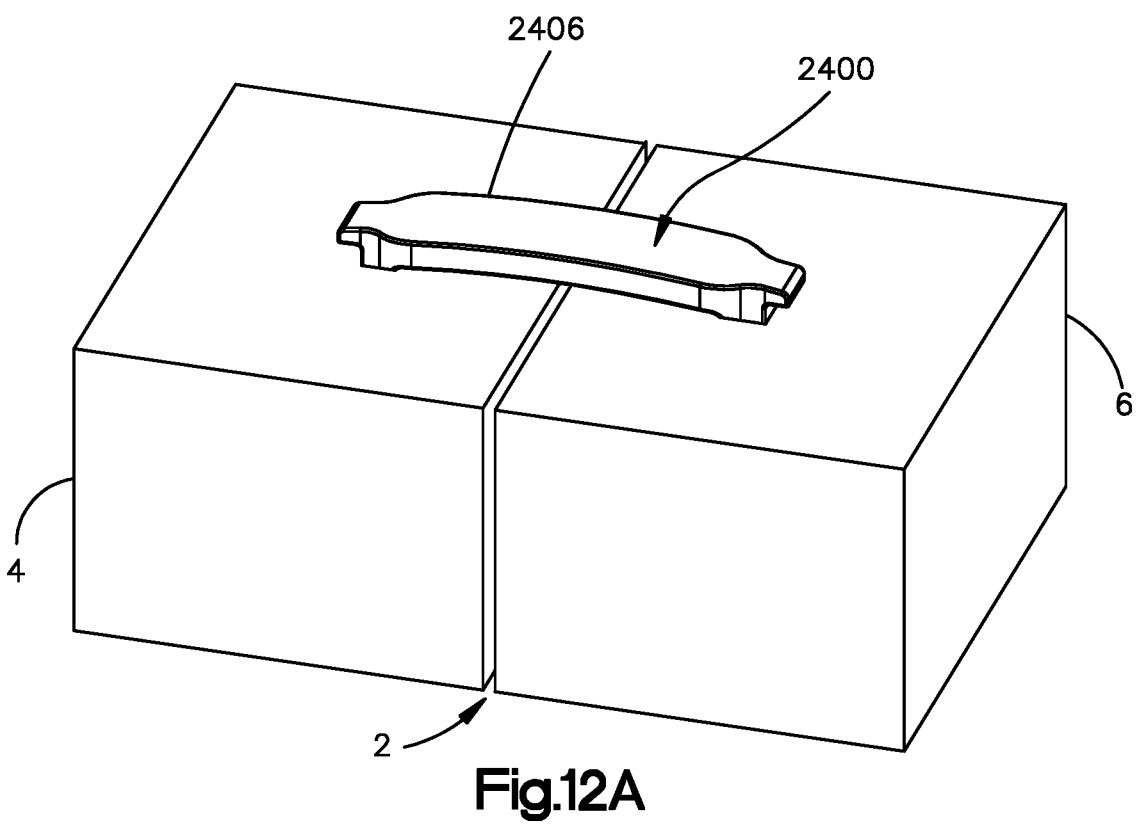
FIG. 12A is a perspective view of a bone fixation clip inserted into bone.
Figure 12B:
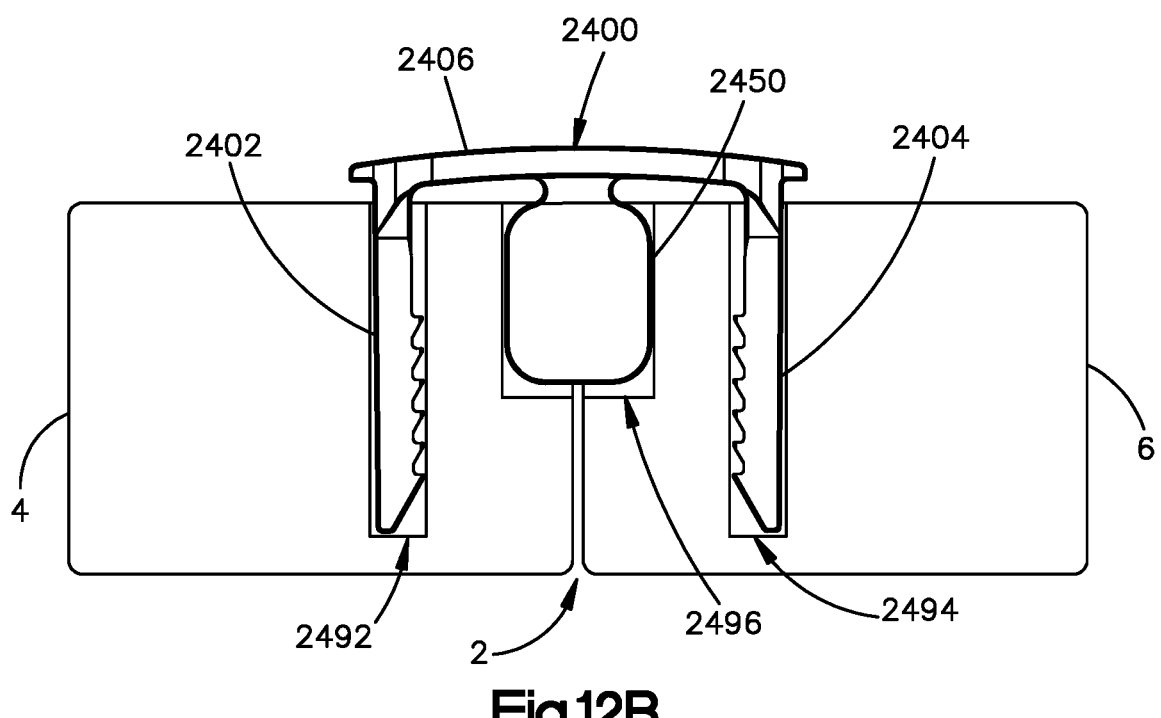
FIG. 12B is a cross-sectional view of a bone fixation clip inserted into bone.

Referring now to FIGS. 12A-12B, the bone implant 2400 may then be inserted into the bones 4 and 6. In particular, the bone implant 2400 can be inserted such that the first leg 2402 of the bone implant 2400 is inserted into the first hole 2492 in which the first guide pin was inserted and subsequently removed, the second leg 2404 of the bone implant 2400 is inserted into the second hole 2494 in which the second guide pin was inserted and subsequently removed, and the keel 2450 is inserted into the third or intermediate hole 2496 created by the surgical saw 240. The first hole 2492 can be localized in the first bone 4, the second hole 2494 can be localized in the second bone 6, and the third or intermediate hole 2496 can extend into each of the first bone 4 and the second bone 6 across the joint 2. The first and second legs 2402 and 2404 of the implant 2400 can be driven into the first and second holes 2492 and 2494 such that the natural biasing force of the implant 2400 causes the legs provide a compressive force to the bones 4 and 6 across the joint 2. The keel 2400 can be disposed in the third hole 2406 across the joint 2. The bridge 2406 can extend from the first leg 2402 to the second leg 2404 across the joint 2. In particular, the bridge 2406 can extend along a direction substantially perpendicular to the joint 2. In this regard, the first and second legs 2402 and 2404 can be separated by a direction that is substantially perpendicular to the joint 2.

The embodiments described herein are exemplary. Modifications, rearrangements, substitute processes, etc. may be made to these embodiments and still be encompassed within the teachings set forth herein. Depending on the embodiment, certain acts, events, or functions of any of the methods described herein can be performed in a different sequence, can be added, merged, or left out altogether (e.g., not all described acts or events are necessary for the practice of the method). Moreover, in certain embodiments, acts or events can be performed concurrently rather than sequentially.

The phrases "connected to," "coupled to," and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together.

Terms relating to circular shapes as used herein, such as diameter or radius, should be understood not to require perfect circular structures, but rather should be applied to any suitable structure with a cross-sectional region that can be measured from side-to-side. Terms relating to shapes generally, such as "circular," "cylindrical," "semi-circular," or "semi-cylindrical" or any related or similar terms, are not required to conform strictly to the mathematical definitions of circles or cylinders or other structures, but can encompass structures that are reasonably close approximations.

The terms "approximately," "about," and "substantially" as used herein represent an amount close to the stated amount that still performs a desired function or achieves a desired result. For example, in some examples, as the context may dictate, the terms "approximately," "about," and "substantially," may refer to an amount that is within less than or equal to 10% of the stated amount. The term "generally" as used herein represents a value, amount, or characteristic that predominantly includes or tends toward a particular value, amount, or characteristic. As an example, in certain examples, as the context may dictate, the term "generally parallel" can refer to something that departs from exactly parallel by less than or equal to 20 degrees. All ranges are inclusive of endpoints.

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements, and/or states are in any way required for one or more embodiments or that one or more embodiments necessarily include logic for deciding, with or without author input or prompting, whether these features, elements and/or states are included or are to be performed in any particular embodiment. The terms "comprising," "including," "having," "involving," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y and/or Z). Thus, such disjunctive language is not generally intended to, and should not, imply that certain embodiments require at least one of X, at least one of Y or at least one of Z to each be present.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B, and C" can include a first processor configured to carry out recitation A in conjunction with a second processor configured to carry out recitations B and C.

While the above detailed description has shown, described, and pointed out novel features as applied to illustrative embodiments, it will be understood that various omissions, substitutions, and changes in the form and details of the devices or algorithms illustrated can be made without departing from the spirit of the disclosure. As will be recognized, certain embodiments described herein can be embodied within a form that does not provide all of the features and benefits set forth herein, as some features can be used or practiced separately from others. All changes which come within the meaning and range of equivalency of the claims are to be embraced within their scope.

What is claimed is:

1. A method of joining two bones, the method comprising:
driving first and second guide pins into respective first and second bones, such that the first and second guide pins are disposed in first and second holes, respectively of the first and second bones;
attaching a saw guide to a surgical saw, the saw guide comprising:
a distal portion that defines first and second guide holes configured to receive the first and second pins, respectively, and a slot positioned between the first and second guide holes configured to receive a saw blade of the surgical saw;
a proximal portion comprising a proximal opening configured to receive a blade attachment assembly on the surgical saw; and
a side-facing opening through which a portion of the blade attachment assembly slides when the blade attachment assembly is inserted into the proximal opening of the saw guide;
wherein attaching the saw guide to the surgical saw comprises inserting the saw blade and blade attachment assembly into the proximal opening of the saw guide prior to sliding the saw guide over the first and second guide pins;
after the driving step, inserting the first and second guide pins into the first and second guide holes, respectively, such that the saw blade of the surgical saw is aligned with a target cut location that is defined by either or both of the first and second bones;
guiding movement of the surgical saw along the first and second guide pins to the target cut location, such that the saw blade creates an intermediate slot at the target cut location between the first and second holes;
removing the surgical saw and the first and second guide pins; and
inserting an implant into the first and second holes, such that a keel of the implant is inserted into the intermediate hole,
wherein the saw guide comprises a side-facing opening through which a portion of the blade attachment assembly slides when the blade attachment assembly is inserted into the proximal opening of the saw guide.

2. The method of claim 1, wherein after the driving steps, the first and second guide pins are disposed in respective first and second bone holes of the first and second bones, such that the step of removing the first and second guide pins exposes the first and second bone holes, and the step of inserting the implant comprises inserting first and second legs of the implant into the first and second bone holes, respectively.

3. The method of claim 2, wherein the implant is inserted in an elastically deformed configuration, such that upon insertion, the first and second legs provide a compressive force between the first and second bones.

4. The method of claim 2, further comprising the step of drilling the first and second bone holes, such that the driving steps comprise driving the first and second guide pins into the first and second bone holes, respectively.

5. The method of claim 4, comprising positioning a drill guide on the first and second bones, the drill guide comprising first and second channels each configured to receive a drill bit, and drilling the first and second bone holes through the first and second channels, respectively.

6. The method of claim 1, wherein the first and second channels are grooves formed into interior sides of the saw guide.

7. The method of claim 1, wherein the saw guide is slid over the first and second guide pins prior to attaching the saw guide to the surgical saw.

8. The method of claim 1, wherein the slot in the saw guide extends continuously from the first guide hole to the second guide hole.

9. The method of claim 1, wherein the first and second bones are defined by anatomically distinct bones.

10. The method of claim 1, wherein the first and second bones are defined by bone fragments of a common anatomical bone.

11. The method of claim 1, further comprising the step of driving a K-wire into a joint between the first and second bones, such that the K-wire is disposed at a K-wire location that extends through the target cut location, and the guiding step comprises creating the intermediate slot that is elongate along a direction that separates the first and second holes after the K-wire has been removed from the joint, and the intermediate slot contains the K-wire location.

12. A surgical saw guide, comprising:
a distal portion that defines first and second guide holes configured to receive first and second pins, respectively, and a slot positioned between the first and second guide holes and configured to receive an oscillating saw blade;
a proximal portion comprising a proximal opening configured to receive a blade attachment assembly of a surgical saw; and
a side-facing opening configured to slidably receive a portion of the blade attachment assembly,
wherein the side-facing opening comprises a proximal portion having linear edges and a distal portion having a curved edge, and a width between opposing curved edges is greater than a width between the linear edges.

13. The surgical saw guide of claim 12, wherein the first and second guide holes open into first and second guide channels, respectively, configured to receive first and second guide pins from the first and second guide holes.

14. The surgical saw guide of claim 12, wherein the side-facing opening and the proximal opening form a continuous opening.

15. The surgical saw guide of claim 12, wherein the slot in the saw guide forms a continuous opening from the first guide hole to the second guide hole.

16. A kit, comprising:
first and second guide pins;
a drill guide comprising a first and second guide holes configured to receive a drill bit and the first and second guide pins; and
the surgical saw guide of claim 12.

* * * * *